United States Patent [19]
Guy et al.

[11] Patent Number: 6,126,938
[45] Date of Patent: Oct. 3, 2000

[54] METHODS FOR INDUCING A MUCOSAL IMMUNE RESPONSE

[75] Inventors: Bruno Guy, Lyons; Jean Haensler, Saint-Genis-les-Ollières; Marie-José Quentin-Millet, Villeurbanne, all of France

[73] Assignee: Pasteur Merieux Serums & Vaccins, Lyons, France

[21] Appl. No.: 09/018,460

[22] Filed: Feb. 4, 1998

Related U.S. Application Data

[63] Continuation of application No. 08/750,449, filed as application No. PCT/FR96/00534, Apr. 9, 1996, abandoned.

[30] Foreign Application Priority Data

Apr. 7, 1995 [FR] France .................................. 95/04433

[51] Int. Cl.⁷ .................................................. A61K 39/00
[52] U.S. Cl. .................... 424/184.1; 424/199.1; 424/234.1; 424/278.1; 424/282.1; 424/812; 514/44
[58] Field of Search .............................. 424/184.1, 199.1, 424/234.1, 278.1, 282.1, 812; 514/44

[56] References Cited

U.S. PATENT DOCUMENTS

| | | | |
|---|---|---|---|
| 5,529,777 | 6/1996 | Andrianov et al. | 424/184.1 |
| 5,538,729 | 7/1996 | Czinn et al. | 424/234.1 |
| 5,679,564 | 10/1997 | Pace et al. | 424/184.1 |
| 5,833,993 | 11/1998 | Wardley et al. | 424/199.1 |
| 5,853,763 | 12/1998 | Tice et al. | 424/234.1 |

FOREIGN PATENT DOCUMENTS

| | | |
|---|---|---|
| 2220211 | 1/1990 | United Kingdom . |
| 9503824 | 2/1995 | United Kingdom . |
| 9106282 | 5/1991 | WIPO . |

OTHER PUBLICATIONS

Nedrud et al, Journal of Immunology, 139, 3484–3492, 1987.
McGhee et al, vaccine, *10*, 75–88, 1992.
Gallichman et al, Jour. infect. Diseases, *168*, 622–629, 1993.

*Primary Examiner*—David Saunders
*Attorney, Agent, or Firm*—Clark & Elbing LLP

[57] ABSTRACT

The invention relates to a pharmaceutical composition intended for inducing in a host mammal a protective immune response against an antigen, at a mucosal effector site, which comprises at least two identical or different products each containing an inducing agent for the immune response, selected from the antigen and, provided the antigen is protein in nature, an expression cassette capable of expressing the antigen, for a concomitant or consecutive administration; one of the products being formulated so as to be administered via the nasobuccal route so that the inducing agent is targeted to the inducer site(s) for an immune response in the naso-oropharynx or the salivary glands, the other product being formulated so as to be administered via a suitable mucosal route other than the nasal route, so that the inducing agent is targeted to the inducer site(s) for an immune response at the effector site at which the immune response is sought. Optionally, such a composition can also comprise a third product, identical to or different from the first two, formulated for systemic administration.

28 Claims, 13 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 41 base pairs
      (B) TYPE: nucleic acid -continued

```
        (C) STRANDEDNESS: double
        (D) TOPOLOGY: linear (ii) MOLECULE TYPE: cDNA (xi) SEQUENCE DESCRIPTION: SEQ ID NO:1:

CCCAAATCAT GAAACTCACC CCAAAAGAGT TAGATAAGTT G                           41

(2) INFORMATION FOR SEQ ID NO:2:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

GCTTCTACAT AGTTAAGCTT AATGCCTT                                          28

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

CGTCTCGAGC CACCATGAAA AAGATTAGCA GAAAAG                                 36

(2) INFORMATION FOR SEQ ID NO:4:

(i) SEQUENCE CHARACTERISTICS:
        (A) LENGTH: 49 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

ATCGTCCCGG GCAGGCCTCT TAGAAAATGC TAAAGAGTTG CGCCAAGCT                   49
```

METHODS FOR INDUCING A MUCOSAL IMMUNE RESPONSE

This application is a continuation of Application No. 08/750,449, filed Jan. 27, 1997, now abandoned which was filed under 35 U.S.C. §371 as a national stage application of PCT/FR96/00534, filed Apr. 9, 1996.

The present invention relates to a vaccination kit for inducing in a mammal a protective immune response against a pathogenic organism which infects mucosae.

The cells of immunity can be concentrated within organs or can form a more or less diffuse lymphoid tissue, these tissues and organs collectively constituting the lymphoid system. Primary lymphoid organs, which are the major sites of lymphopoiesis (thymus, bone marrow), and secondary lymphoid organs and tissues, within which the lymphocytes can interact with one another or with the antigen, are recognized. The secondary lymphoid organs comprise, among others, the spleen, the lymph nodes and the lymphoid formations associated with the mucosae (MALT for mucosal associated lymphoid tissue), Peyer's patches and palatine tonsils. In addition to the organized lymphoid tissue constituting the MALT, a large number of lymphocytes are found in the mucosa of the stomach, of the small intestine, of the colon, of the bronchi and of various other organs.

After differentiating in the primary lymphoid organs, the lymphocytes migrate to the secondary lymphoid organs. The latter can be inducer sites for systemic immunity or for mucosal immunity. They may thus be referred to as "systemic" or "mucosal" organs.

Among the "systemic" organs, the spleen, which responds to antigens that enter the blood circulation, and the peripheral nodes, which provide for protection against antigens that enter the anatomical region for which they effect lymphatic drainage, are recognized. A list of the different nodes in relation to the regions which they drain (inducer or effector sites) is presented in the Table below.

The immune system associated with the mucosae, for its part, protects the body against antigens that enter via the mucosal epithelial surfaces and reside hereon. This includes Waldeyer's ring and lymphoid issues are found associated with the respiratory tract (BALT for bronchial associated lymphoid tissue), with the digestive tract (GALT for gut associated lymphoid tissue) and with the urogenital tract. The immune system associated with the mucosae (inducer sites) is presented in FIGS. 11–13.

Once stimulated in the inducer secondary organs, the lymphocytes can migrate to the effector sites conveyed by the lymph, via the nodes associated with the inducer sites, where appropriate via the larger nodes draining these first nodes, the effluent lymphatic venules ending in the thoracic duct. The lymph from the latter joins the blood circulation, through which the cells make their way to the target organs or effector sites. As regards the lymphoid cells of the MALT, the latter recirculate to the mucosal areas. For example, cells stimulated in the Peyer's patches pass through the associated nodes and then into the blood to become localized in certain mucosal sites. This selective recirculation is due to the capacity of lymph sites to recognize adhesion molecules expressed specifically on the endothelial cells of the post-capillary venules of the mucosae. As a result of this mechanism, the antigenic stimulation of a mucosal area (inducer) can induce a response in other mucosal areas (effectors).

To date, numerous methods of immunization have been reported in the scientific literature. The key features of these methods are, generally speaking, (i) the nature of the immunogen, (ii) the route or routes of administration of the immunogen, and also (iii) the formulation of the immunogen.

As regards the nature of the immunogen, the possibility of using an immunogen which is nucleic acid in nature (RNA, DNA) as an alternative to an antigen which is protein in nature has already been known for a long time. There is hence no need to elaborate further upon this aspect.

The immunization routes and methods that favour the prevention or treatment of mucosal infections have already been the subject of a number of studies but, despite this, they have not met with as much success as the vaccination against systemic infections.

Nevertheless, these studies collectively indicate that, when a pathogen that establishes itself in the mucosae is involved, immunization by systemic administration does not appear to be sufficient on its own for an adequate protection to be developed. It appears desirable if not essential to induce an immunization by mucosal administration, possibly in addition to an immunization by systemic administration, in order to combat this type of infection with efficacy. Immunization by mucosal administration makes it possible in essence to stimulate the lymphoid tissue draining the mucosa(e) where the pathogen is lodged, and thus to obtain an immune response targeted at this/these mucosa(e).

Type A immunoglobulins (IgA) constitute the majority of the immunoglobulins at the surface of the gatrointestinal, respiratory, urogenital or other mucosae. They are secreted within these mucosae and deemed to confer protection against infections affecting these sites.

A mucosal immune response is normally obtained after immunization by mucosal administration, either directly at the effector mucosa or at another mucosal site at a distance from the site at which the infection is to be combated. The mucosal routes which are in principle accessible for immunization are the oral route, the intragastric route, the nasal route, the urogenital route and the rectal route. However, the oral route is the one on which the choice preferentially falls, on account of its ease of use, whether for vaccinating against infections of the gastrointestinal mucosa or for vaccinating against infections affecting another mucosa.

To illustrate this point, various examples of the prior art are given as follows:

Recently, Czinn et al., Vaccine (1993) 11 : 637 have proposed in outline a method of vaccination against *Helicobacter pylori*, the pathogenic agent of a large number of stomach ulcers. Germ-free mice received a sonicate of *H. felis* with cholera toxin as adjuvant, via the intragastric route (sonicate administered directly by intubation into the stomach). After a challenge with *H. felis*, the immunized mice are found to have been protected.

This procedure is referred to for convenience in the remainder of the paper as "oral immunization". The equivalent of this paper is to be found in the Czinn & Nedrud Patent Application WO 93/20,843.

Jertborn et al., Vaccine (1992) 10 : 130 report a study of cholera vaccination performed with a small group of Swedish subjects. The vaccine was administered in two doses, in the form of a liquid solution to be swallowed. This vaccine proved both effective and risk-free.

Vaccination against influenza via the nasal route has been carried out successfully in children and adults, as reported by Anderson et al., J. Clin. Microbiol. (1992) 30 : 2230 and Treanor et al., Ann. Inter. Med. (1992) 117 : 625.

Gallichan et al., J. Infect. Dis. (1993) 168 : 622 shows that it is possible to induce both a mucosal and a systemic immune response after intranasal administration of a recombinant adenovirus expressing herpes simplex virus (HSV) glycoprotein B. In conclusion, the authors suggest that, generally speaking, their approach would enable a long-term protection against mucosally or sexually transmitted viruses to be obtained.

Some studies, such as Forest et al., Vaccine (1990) 8 : 209, suggest that the rectal route could be an entry route common to the whole of the mucosal immune system, and that it should be possible to induce a mucosal immune response at a site distant from the rectal mucosa, used as entry route for the immunogen.

The combination of different immunization routes has already been described by several authors as being a means of choice for obtaining an optimal response. The combination of a mucosal administration and a systemic administration is, for example, described in the following papers.

Keren et al., Infect. Immun. (1988) 56 (4) : 910 show that a method of immunization by combined routes, parenteral and oral, gives better results in terms of IgA response against *Shigella flexneri* than an immunization via a single route. In practice, mice receive the antigen intramuscularly and intragastrically by means of a tube, under anaesthesia.

Yoshimura et al., Arch. Otolaryngol. Head Neck Surg. (1991) 117 : 889 propose vaccination against pneumococcal otitis by combining systemic and oral administrations. The immunization protocols are tested in guinea pigs. The so-called oral administration is performed, in fact, in the duodenum or the stomach by means of a catheter, or alternatively consists in the taking of enteric capsules. The authors show that only the combination of systemic administration+oral administration in the form of capsules gives good results.

Forest et al., Infect. Immun. (1992) 60 (2) : 465 test several modes of immunization in man for the purpose of inducing an IgA response against *Salmonella typhi*. The oral and subcutaneous routes are used as follows: oral; oral/oral; oral/subcutaneous; and subcutaneous/oral. The authors show that a first parenteral injection followed several days later by a second dose taken orally does not promote the IgA response. In contrast, taking the vaccine orally, repeated once, gives good results.

Hartman et al., Infect. Immun. (1994) 62 (2) : 412 describe several protocols for immunization against Shigella. One of them in particular comprises a first intraperitoneal or subcutaneous injection followed by a booster via the ocular route. This protocol is tested in the guinea pig model of keratoconjunctivitis. The authors show that, in naive animals, immunization by mucosal administration is necessary for the induction of protection. Double immunization, parenteral and mucosal, increases the level of protection.

Nedrud et al., J. Immunol. (1987) 139 : 3484 describe a method of immunization against Sendai virus infections (infections of the nasopharynx which can possibly progress to bronchitis and pneumonia). The effector site at which the immune response could be sought by carrying out this method is hence the whole of the respiratory tract. The method of Nedrud et al. comprises two major steps: an oral (intragastric) primary immunization and a booster via the nasal route. Generally speaking, the oral (intragastric) route is considered not to be the optimal route for enabling an inducing agent (in this case the Sendai virus) to reach one of the inducer sites for an immune response in the respiratory tract.

It has now been found that an immune response at a mucosal site of any kind and against an antigen of any kind could be greatly promoted by implementing an immunization protocol combining several routes.

Accordingly, the present invention relates to a pharmaceutical composition for inducing in a host mammal a protective immune response against an antigen, at a mucosal effector site, which comprises at least two identical or different products each containing an immune response inducing agent, selected from the antigen and, provided the antigen is a protein, an expression cassette capable of expressing the antigen, for a concomitant or consecutive administration; one of the products being formulated so as to be administered via the nasobuccal route so that the inducing agent is targeted to the inducer site(s) for an immune response in the naso-oropharynx or the salivary glands, the other product being formulated so as to be administered via a suitable mucosal route other than the nasal route, so that the inducing agent is targeted to the inducer site(s) for an immune response at the effector site at which the immune response is sought.

Optionally, the pharmaceutical composition according to the invention comprises a third product, identical to or different from the first two, which contains an immune response inducing agent, selected from the antigen and, provided the antigen is protein in nature, an expression cassette capable of expressing the antigen, and which is formulated for systemic administration, preferably before the first two products already mentioned.

In other words, the subject of the invention is a kit for inducing in a host mammal a mucosal immune response against an antigen, at an effector site, which comprises:

(i) optionally, a first immune response inducing agent, selected from the antigen and, provided the antigen is a protein, an expression cassette capable of expressing the antigen, a DNA or RNA fragment coding for the antigen; and (ii) a second and a third inducing agent for the immune response, selected from the antigen and, provided the antigen is protein in nature, an expression cassette capable of expressing the antigen, a DNA or RNA fragment coding for the antigen; with (a) optionally, instructions for the systemic administration of the first inducing agent, (b) instructions for the nasobuccal administration of the second inducing agent, (c) instructions for the administration of the third inducing agent via a suitable mucosal route other than the nasal route, so that the antigen is targeted to the inducer site(s) for the immune response at the effector site at which the immune response is sought, and (d) instructions for the concomitant or consecutive administration of the first, second and third inducing agents.

The invention also relates to a method for inducing in a host mammal an immune response against an antigen, at a mucosal effector site, according to which, in any order:

(i) a first immune response inducing agent, selected from the antigen and, provided the antigen is protein, an expression cassette capable of expressing the antigen, a DNA or RNA fragment coding for the antigen, is optionally administered systemically to the host mammal;

(ii) a second immune response inducing agent, selected from the antigen and, provided the antigen is a protein, an expression cassette capable of expressing the antigen, a DNA or RNA fragment coding for the antigen, is administered via the nasal and/or buccal (nasobuccal) route to the host mammal; and (iii) a third immune response inducing agent, selected from the antigen and, provided the antigen is protein in nature, an expression cassette capable of expressing the antigen, a DNA or RNA fragment coding for the antigen, is administered to the host mammal via the suitable mucosal route other than the nasal route, so that the antigen is targeted to the inducer site(s) for the immune response at the effector site at which the immune response is sought.

The administration of the first inducing agent may advantageously be carried out in a single dose, by systemic injection, such as an intravenous, intramuscular, intradermal or subcutaneous injection. The choice of injection site and route will depend, in particular, on the lymph nodes which it is desired to target. It may be noted that if it is desired, for example, to target the coeliac nodes, it is preferable to perform the injection in the dorsolumbar region using the intramuscular route (rather than the subcutaneous route). It is preferable for this inducing agent to be in particulate form. The inducing agent is advantageously supplemented with an adjuvant, either by precipitation or by adsorption. The adjuvant can be any traditional adjuvant of the aluminium phosphate or hydroxide or calcium phosphate type, or alternatively an adjuvant such as polyphosphazene. It can also be an adjuvant of the liposome, microsphere, ISCOM or virus-like particle (VLP) type; it being especially advantageous to use the latter when it is desired to target the nodes which drain the urogenital region. All these adjuvants are familiar to a person skilled in the art. The appropriate dosage varies in accordance with certain parameters, for example the individual being treated or the nature of the inducing agent. On a point of information, it may be noted that a dose of an antigen can vary from 5 to 100 $\mu$g, preferably from 25 to 50 $\mu$g.

By "Nasobuccal route" is meant, for the purposes of the present invention, the route which enables an immunogen to reach essentially the Waldeyer ring or its equivalent, the nasal-associated lymphoid tissue (NALT) in species other than the human species. It should be clear that the nasobuccal (or buccal) route is not to be confused with what is commonly referred to as the "oral route" and which should be more appropriately designated "intragastric route".

The oral route, including the intragastric route, should enable the inducing agent (antigen) to reach predominantly the mucosae of the lower regions (digestive tract and mainly the small intestine and the Peyer's patches), while the buccal route conveys the inducing agent essentially to the mucosae of the upper regions. The entry site of the buccal route and that of the oral route can be the same; in this case, the entry site is the mouth. Nevertheless, the pathways are essentially different.

The same comment applies in the case of the pulmonary route, which enables the inducing agent to reach the mucosae of the middle regions (bronchi).

For the purpose of optimizing the immune response which is desired, the formulation of the immunogen is also of importance. Generally speaking, it has already been shown that a particulate antigen is more effective in inducing a mucosal immune response than a soluble antigen.

The route which will be followed by the inducing agent starting from an identical entry site will depend on several factors; inter alia, on the nature and size of the particles in the form of which the inducing agent is to be presented, and on the apparatus, advantageously spray or aerosol, which is used to propel the particles, especially on its shape, its directional jet and the speed of propulsion.

As regards the nature of the particles, a person skilled in the art has a large choice at his disposal; this choice, though not limiting, is advantageously made from between two groups: liposomes and microspheres. The methods of preparation of these particles are conventional, and it is within the capacity for a person skilled in the art to select one of them according to his own requirements and to determine the size of the particles which must be appropriate for the inducing agent to be conveyed according to the route which has been adopted and distributed optimally at the target mucosa.

Thus, a particle diameter of less than 10 μm is proposed for administration via the nasal or buccal route; for administration via the pulmonary route, a diameter of 0.05 to 10 μm, preferably of 0.05 to 5 μm; for administration via the oral route, a diameter of 0.05 to 10 μm, preferably of 0.05 to 5 μm.

The main effector sites at which an immune response may be sought are the respiratory system (bronchi, nasopharynx, lungs), stomach, intestine and urogenital system. In the case of the respiratory system, the third inducing agent will advantageously be formulated for administration via the pulmonary route (e.g. liposomes, microspheres, and the like). In the case of the stomach or intestine, the third inducing agent will advantageously be formulated for administration via the oral route including the intragastric route (e.g. in the presence of an enteric protection, such as liposomes, microspheres, bicarbonate or gelatin capsule). In the case of the intestine or the urogenital system, the third inducing agent will advantageously be formulated for administration via the urogenital route, for example in the form of a vaginal capsule, or via the rectal route, for example in the form of a suppository.

The second or third inducing agent may, in addition, be supplemented with an adjuvant other than liposomes or microspheres and lacking toxicity, other than the non-toxic subunits or the detoxified forms of bacterial toxins.

According to a preferred embodiment, the major lipopolysaccharide (MPLA: major lipopolysaccharide antigen) of a bacteria, for example of *E. coli, Salmonella minnesota, Salmonella typhimurium* or *Shigella flexneri,* is used as adjuvant for the second or third inducing agent.

In effect, it has now been found that this type of compound has good adjuvant properties where immunization is to be carried out via the mucosal route.

Accordingly, another aspect of the invention covers the use of MPLA as mucosal adjuvant for the preparation of a composition (i) containing an antigen or, provided the antigen is protein in nature, an expression cassette capable of expressing the antigen, a DNA or RNA fragment coding for the antigen, (ii) for inducing a mucosal immune response against the antigen, and (iii) for administration via the mucosal route.

As a guide, it may be mentioned that the second or third inducing agent, when the latter is an antigen, may be administered at the rate of 100 μg to 1 mg per dose.

According to a preferred embodiment, the first inducing agent (systemic administration), when administered, is administered as a primary injection, allowing a period of 7 to 45 days, preferably 20 to 30 days, to elapse before the first booster (administration of the second or third inducing agent).

According to an alternative embodiment, the first inducing agent may also be administered at the same time as the second or third inducing agent.

The second and third inducing agents may be administered concomitantly or consecutively. When administered interspersed by a period of time, they are advantageously administered at an interval of 7 to 45 days, preferably 28 days.

If necessary, it is also possible to envisage administering the first and second inducing agents simultaneously (that is to say approximately on the same day), and repeating this operation once after an interval of several days.

The choice of each of the three inducing agents is made independently of one another. Advantageously, at least one of the three should be the antigen. It is fairly common for these three inducing agents to be the same and, in this case, it will advantageously be the antigen.

As an alternative to an antigen which is protein in nature, it is also possible to use (i) either a vaccinal vector, e.g. of a pox virus or adenovirus type containing a DNA fragment coding for this antigen and placed under the control of a suitable promoter, (ii) or this DNA fragment as such (not carried by a vaccinal vector), put into plasmid form or otherwise (preferably the DNA fragment will be inserted into a plasmid instead of remaining in the state of a simple transcription unit), presented in an (anionic or cationic) liposomal formulation or otherwise, (iii) or alternatively the corresponding RNA fragment. These possibilities have already been described in the literature.

In order to implement any one of the different possibilities mentioned in the preceding paragraph, a promoter is used capable of inducing in mammalian cells the expression of the DNA fragment coding for the antigen. For vaccines commonly referred to as DNA-based (in order to differentiate them-from vaccines based on viral vectors), the human cytomegalovirus (hCMV) early promoter is a promoter of choice. For this type of vaccination, it will be preferable to use a plasmid incapable of replicating in mammals. It is also appropriate for such a plasmid to be essentially non-integrative.

According to a preferred embodiment, the antigen of a bacterium which is pathogenic for the host mammal is an *H. pylori* antigen, for example the apoenzyme form of *H. pylori* urease or one of the subunits ureA or ureB of this same urease.

More generally from the standpoint of the method of immunization, and at the same time more precisely targeted from the standpoint of the antigen, it may be pointed out that the subject of the invention is also the use of a DNA fragment coding for an *H. pylori* antigen in the manufacture of a composition for preventing or treating an *H. pylori* infection, and for nasal or nasobuccal administration. To this end, the DNA fragment used as vaccination agent meets the criteria stated above.

It was also found that, in order to induce a mucosal immune response against a pathogenic organism infecting the stomach or intestine, it would not be essential to administer an immunogen at one of these sites, but could be sufficient to administer it via the upper route, that is to say via the nasobuccal route, where appropriate combining a systemic administration therewith.

Accordingly, in another aspect, the invention relates to a composition for inducing in a host mammal an immune response against an antigen, in the stomach or intestine, which comprises an inducing agent for the immune response, selected from the antigen and, provided the antigen is protein in nature, an expression cassette capable of expressing the antigen, a DNA or RNA fragment coding for the antigen, the inducing agent being formulated so as to be administered via the nasobuccal route.

In this same aspect, the invention also covers the use of a product selected from an antigen and, provided the antigen is protein in nature, an expression cassette capable of expressing the antigen, a DNA or RNA fragment coding for the antigen, for the preparation of a composition for inducing in a host mammal an immune response against the product, in the stomach or intestine, and for administration via the nasobuccal route.

Such a composition, when it comprises an antigen of a pathogenic organism which infects the gastric or intestinal mucosa, is useful, in particular, in that it protects the host mammal against the infection in question, in particular affording long-lasting protection, bringing into play memory T and B lymphocytes. Possible infections are those caused by *H. pylori, V. cholerae, Shigella flexneri, Shigella sonnei, Salmonella enteritidis, Clostridium difficile, Yersinia enterocolitica*, and enterotoxigenic and enteropathogenic *E. coli*. As regards the antigen, the latter can be the pathogenic agent itself in killed, lysed or attenuated form, or alternatively antigenic components of this pathogen, such as a capsular polysaccharide, or membrane antigens in purified form, or a polypeptide characteristic of this pathogen, either directly purified from the pathogen or obtained by recombinant DNA techniques.

For example, in the case of a composition for preventing *H. pylori* infections, an antigen of choice may be the apoenzyme of the urease, composed of the subunits A and B, for which the corresponding DNA fragments are described in, e.g., Labigne et al., J. Bact. (1991) 173 (6) : 1920, or one of the subunits of the apoenzyme, or the cytotoxin (WO93/18150), or alternatively proteins of the adhesin family (proteins capable of binding to the receptors of the host cells and which become capable of mediating a coupling of the pathogen to the host cells and of initiating the infectious process), or iron-regulated proteins.

In the case of a cholera vaccine, an antigen of choice can be cholera toxin subunit B, as described in the literature.

The invention is illustrated below by reference to FIGS. 1 to 5.

FIG. 1 depicts the Elispot analysis of the immune response induced by administration of cholera toxin subunit B (CTB) into the salivary glands (1A) and into the stomach (1B). The results relate to three immunization protocols: subcutaneous/oral (Sc O); subcutaneous/nasal (Sc N); and subcutaneous/oral+nasal (Sc O+N). "Oral" is, of course, understood to mean "intragastric". The heavy shading on a light background corresponds to the IgA response. The light shading on a dark background corresponds to the IgG2a response. The response in the stomach is presented as the number of responding mice in a group of 5 mice; the number of spots per million cells is of the order of 9.

FIG. 2 depicts the Elispot analysis of the immune response induced in the salivary glands (2A) and in the stomach (2B) by administration of CTB according to the subcutaneous/subcutaneous+oral+nasal (Sc/Sc+C+N) protocol. "Oral" is, of course, understood to mean "intragastric". The heavy shading on a light background corresponds to the IgA response. The light shading on a dark background corresponds to the IgG2a response. The response in the stomach is presented as the number of responding mice in a group of 5 mice; the number of spots per million cells is of the order of 8.2.

FIG. 3 depicts the Elispot analysis of the immune response induced in the salivary glands (3A) and in the stomach (3B) by administration of jack bean urease according to the subcutaneous (alum)/oral+nasal (liposome) protocol. "Oral" is, of course, understood to mean "intragastric". The heavy shading on a light background corresponds to the IgA response. The light shading on a dark background corresponds to the IgG2a response. The response in the stomach is presented as the number of responding mice in a group of 5 mice; the number of spots per million cells is of the order of 620.

FIG. 4 depicts the Elispot analysis of the immune response induced in the salivary glands (4A) and in the stomach (4B) by administration of jack bean urease according to the subcutaneous (liposomes)/oral+nasal (liposomes) protocol. "Oral" is, of course, understood to mean "intragastric". The heavy shading on a light background corresponds to the IgA response. The light shading on a dark background corresponds to the IgG2a response. The response in the stomach is presented as the number of responding mice in a group of 5 mice; the number of spots per million cells is of the order of 15.

Figure 9:
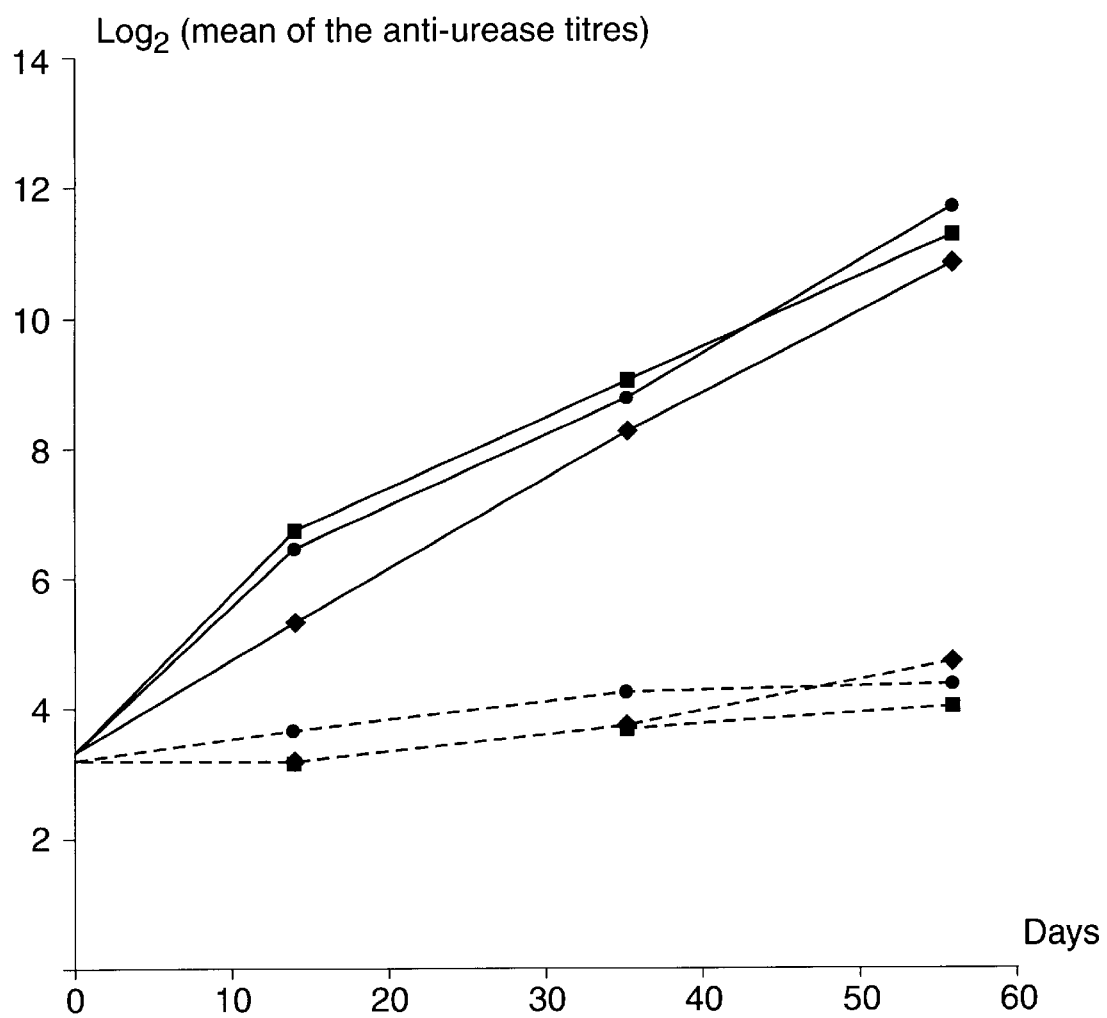

FIG. 9 shows in diagrammatic form the anti-urease antibody titres recorded in Balb/c mice immunized with plasmid pCB-ureB. The continuous curves depict the IgG titres and the broken curves, the IgA titres. p corresponds to an immunization via the intranasal route repeated three times (DO, 21 and 42; plasmid alone or plasmid+liposomes). ♦ corresponds to a primary immunization via the intramuscular route (plasmid alone), followed by two boosters on D21 and 42 via the intranasal route (plasmid+liposomes). • corresponds to a primary immunization via the intradermal route (plasmid alone), followed by two boosters on D21 and 42 via the intranasal route (plasmid+liposomes).

Figure 10:
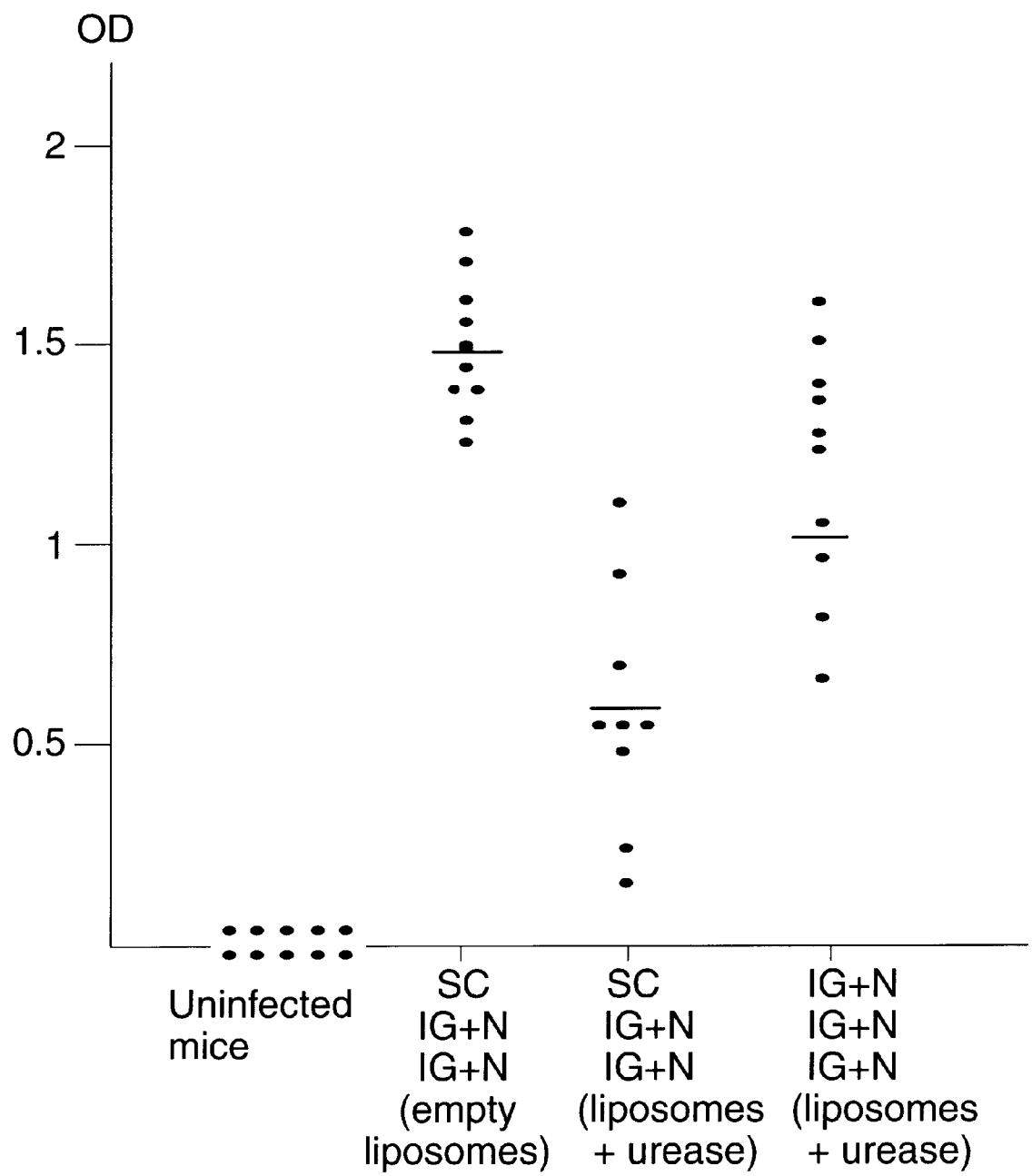

FIG. 10 depicts in diagrammatic form the optical density of the gastric medium of mice after immunization, where appropriate, with the apoenzyme of *H. pylori* urease and challenge. First column: uninfected mice; second column: mice which have received empty liposomes, by subcutaneous primary immunization followed by two boosters via the (nasal+intragastric) routes; third column: mice which have received liposomes with urease, by subcutaneous primary immunization followed by two boosters via the (nasal+intragastric) routes; fourth column: mice which have received liposomes with urease, by administration repeated three times via the (nasal+intragastric) routes. In all cases, DC-Chol liposomes are used.

Figure 11:
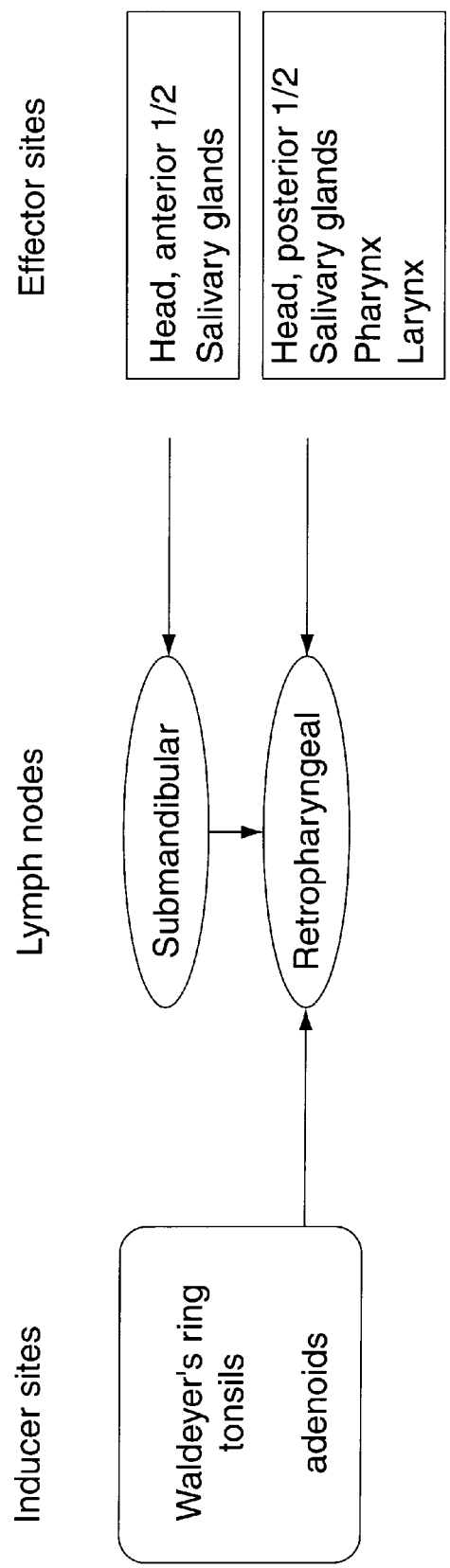
Figure 12:
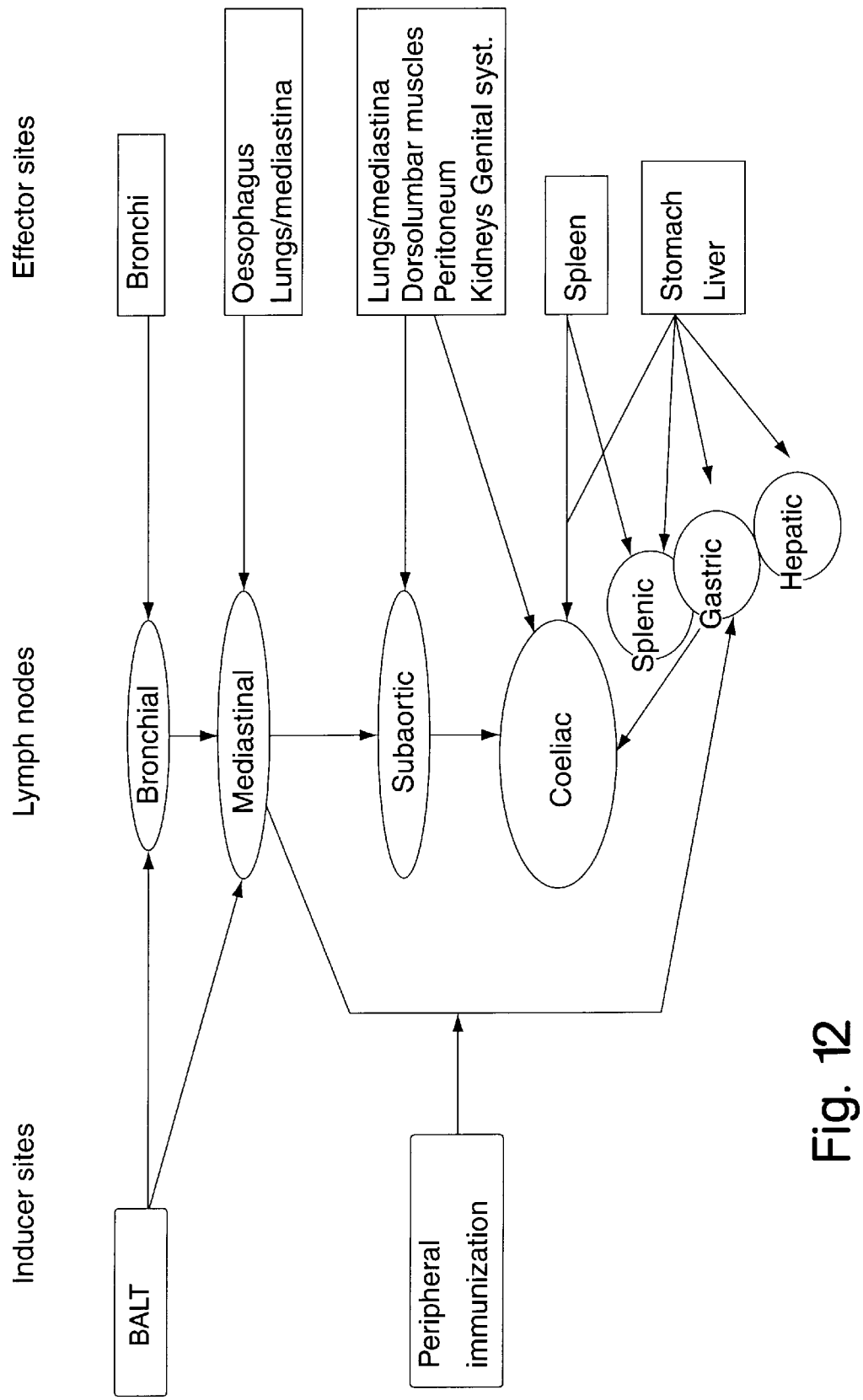
Figure 13:
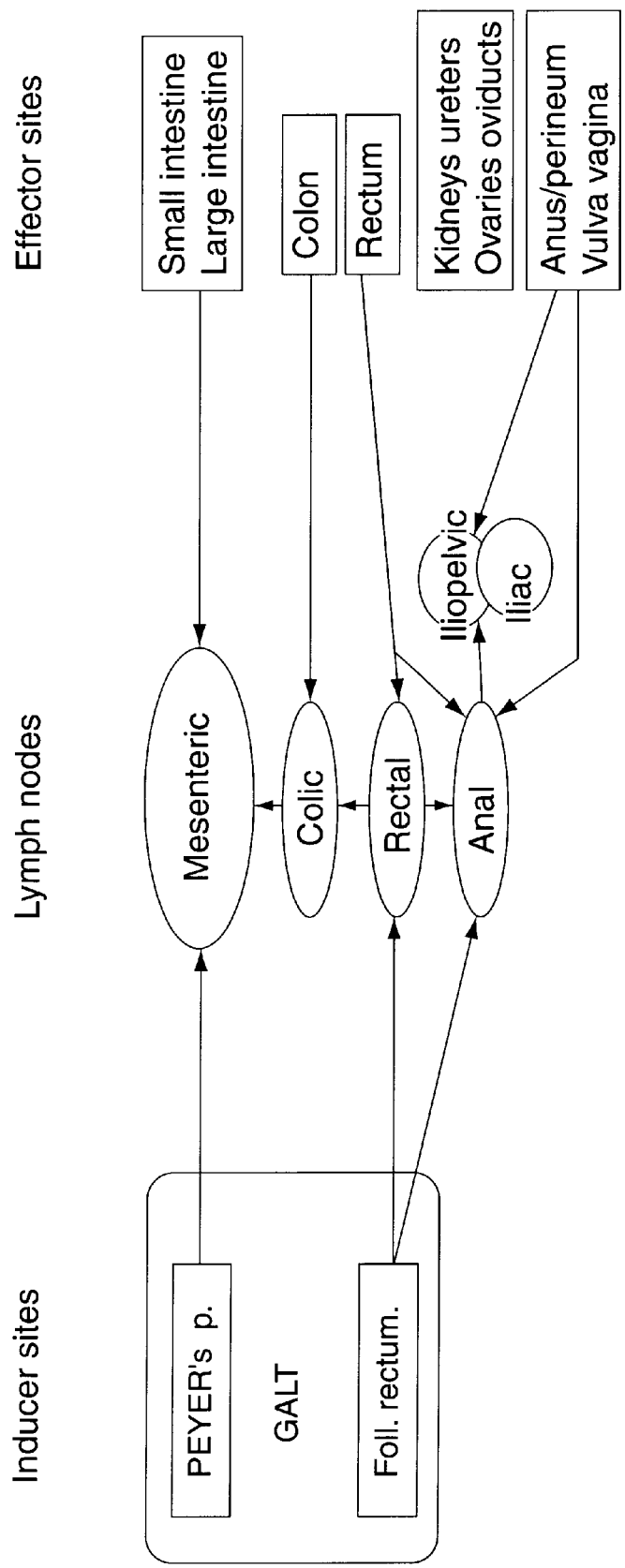

FIGS. 11, 12, and 13 provide a schematic illustration of the immune system associated with the mucosae (inducer sites).

EXAMPLE 1

Induction of a mucosal immune response against cholera toxin subunit B (CTB)

1.A. Preparation of the immunizing compositions

1.A.a) For administration via the subcutaneous route

1 μl of a preparation of CTB purified and concentrated to 10 mg/ml (equivalent to 10 μg of CTB) is mixed with 100 μl of a 1% aluminium hydroxide preparation. The mixture is diluted in PBS buffer to obtain a final volume of 500 μl. This constitutes one individual dose.

1.A.b) For administration via the oral (intragastric) route

A volume of 3 μm latex beads (Polysciences cat. 17 34) is withdrawn and then washed 3 times in PBS buffer (centrifugation 1,000 rpm for three minutes). The beads are then mixed with a preparation of CTB purified and concentrated to 10 mg/ml so as to obtain a preparation in which the CTB is diluted to ½0 (equivalent to a final concentration of 0.5 mg/ml). This preparation is left stirring for 2 hours.

The preparation is then diluted to ½5 with 200 μM carbonate buffer.

1.A.c) For administration via the nasal route

A preparation of CTB coated on latex beads is obtained as described in Section 1.A.b), except for the final dilution in carbonate buffer.

The preparation is then diluted in PBS buffer according to requirements.

1.1.d) For administration via the oral+nasal route

The administration is carried out by combining the oral and nasal administrations as are described in 1.A.b) and 1.A.c).

1.B. Immunization protocol

Three immunization protocols are compared. They are:
1) Subcutaneous/oral (intragastric)
2) Subcutaneous/nasal
3) Subcutaneous/oral (intragastric)+nasal BalbC mice receive via the subcutaneous route 10 μg of CTB with aluminium as adjuvant as described in Section 1.A.a), in a volume of 500 μl.

Mice forming a control group receive 500 μl of PBS subcutaneously.

28 days after the subcutaneous injection, the test mice are divided into 3 groups.

The mice in the first group receive intragastrically, via a cannula coupled to a 1 ml syringe, 10 μg of CTB coated on latex beads as described in Section 1.A.b) in a volume of 500 μl. Mice taken from the control group receive 500 μl of carbonate buffer via the same route.

The mice in the second group receive via the nasal route 10 μg of CTB coated on latex beads as described in Section 1.A.c), in a volume of 20 μl. These 20 μl are applied dropwise to the nostrils. Mice taken from the control group receive 20 μl of PBS via the same route.

The mice in the third group receive simultaneously 10 μg of CTB via the oral (intragastric) route and 10 μg of CTB via the nasal route. The preparation of CTB coated on latex beads is obtained as described in Section 1.A.d). Some mice are used as controls.

15 days after the booster, the stomach and the salivary glands of the mice are removed; the cells are extracted according to the protocol described in Mega et al., J. of Immunology (1992) 148 : 2030, and the IgA response is subjected to Elispot analysis according to the method described in Czerkinsky et al., in Theoretical and Technical aspects of ELISA and other Solid Phase Immuno Assays (D. M. Kenneny and S. J. Chalacombe Eds): 217–239, John Wiley & Sons, Chichester, N.Y.

Figure 1A:
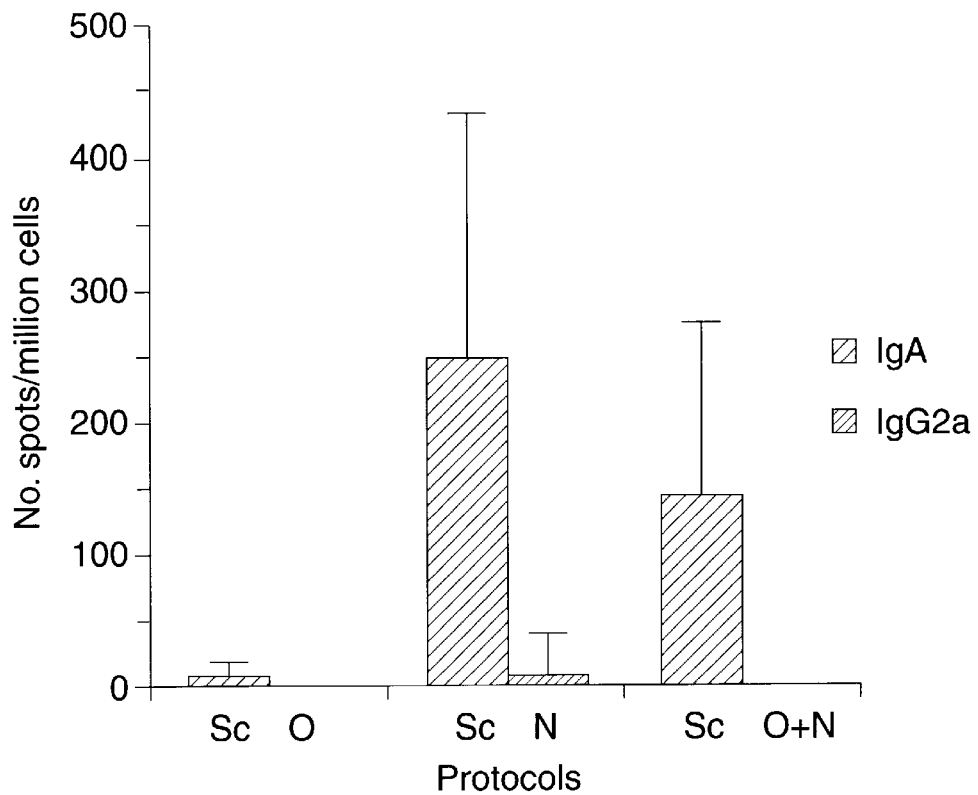
Figure 1B:
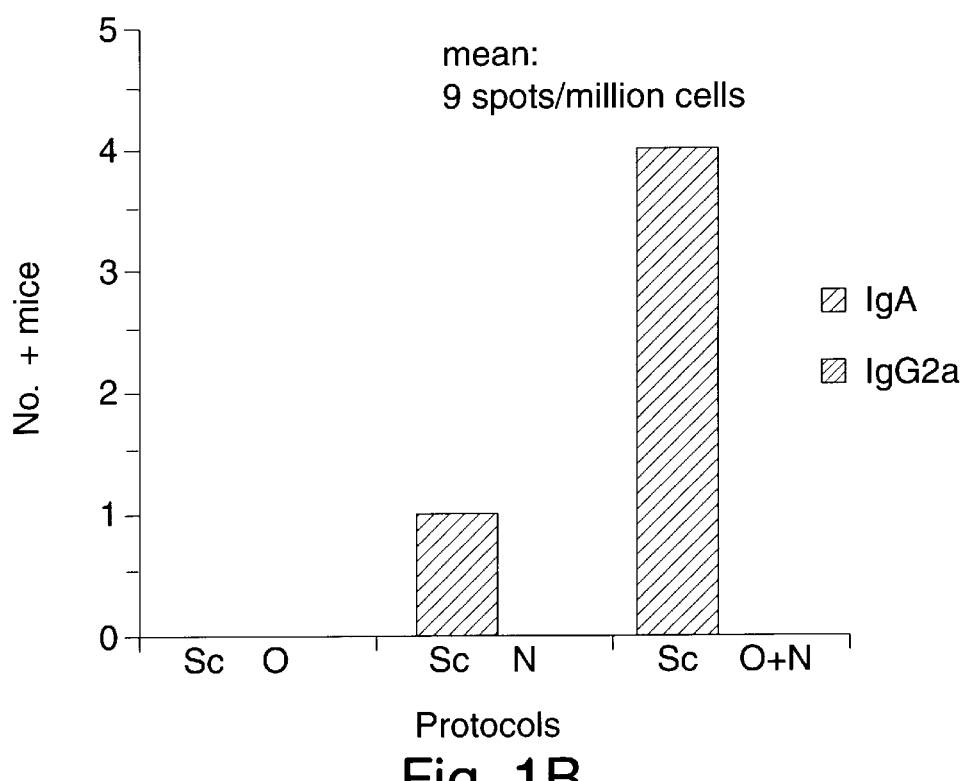

The results are presented in FIG. 1 and prompt the following comments:

The subcutaneous/oral (intragastric) protocol proves incapable of inducing a strong mucosal immune response, while such a response is observed in the case of the subcutaneous/nasal and subcutaneous/oral (intragastric)+nasal protocols.

The latter protocol proves to be the best, inasmuch as a good local response represented by the IgA is obtained both in the salivary glands and in the stomach.

I.C. Supplementary immunization protocol

Mice which have received a subcutaneous injection of CTB as described in Section 1.B. receive 28 days later, simultaneously:

40 μg of CTB as prepared in Section 1.A.d), via the oral (intragastric) route, in a volume of 500 μl;

10 μg of CTB as prepared in Section 1.A.d) via the nasal route, in a volume of 20 μl;

10 μg of CTB as prepared in Section 1.A.a) via the subcutaneous route, in a volume of 300 μl.

Figure 2A:
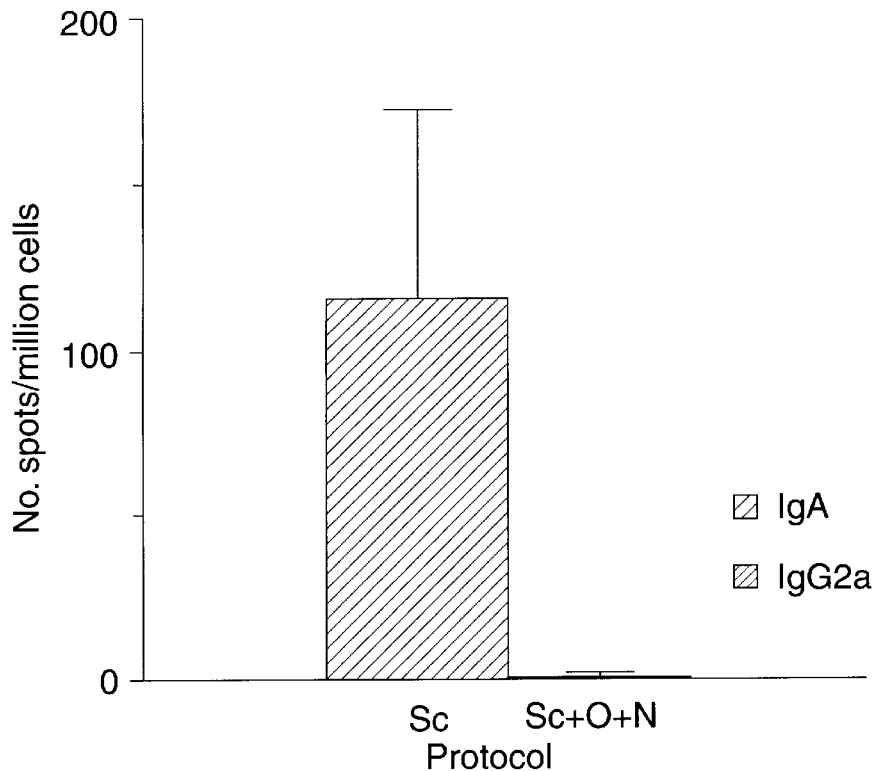
Figure 2B:
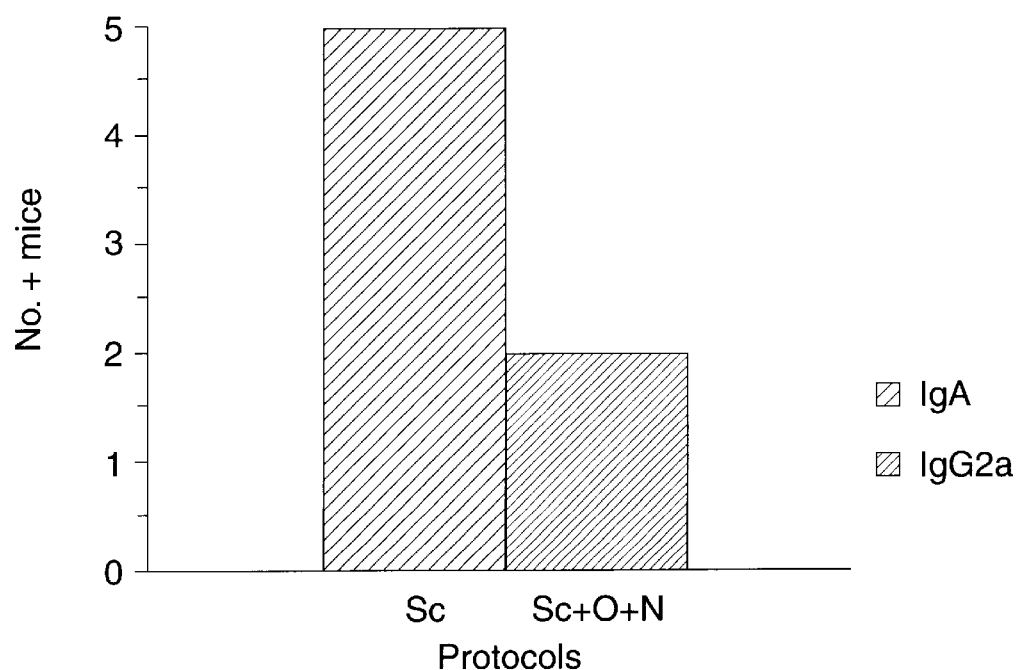

15 days after the booster, the stomach and the salivary glands of the mice are removed; the cells are extracted and the IgA response is subjected to Elispot analysis. The results are presented in FIG. 2. A good IgA type immune response is obtained (⅗ mice respond), this being an index of a local immune response in the mucosae.

EXAMPLE 2

Induction of a mucosal immune response against jack bean urease

2.A. Preparation of the immunizing composition

2.A.a) urease with aluminium as adjuvant

5 μl of a jack bean urease preparation (Boehringer; ref 737 348) concentrated to 4 mg/ml in PBS buffer are mixed with 100 μl of a 1% aluminium hydroxide preparation. The mixture is diluted in PBS buffer to obtain a final volume of 500 μl containing 20 μg of urease. This constitutes one individual dose.

2.A.b) urease in liposomes

Three techniques are used, as follows:

1. Injection of ethanol 16.4 mg of a lipid mixture composed of cholesterol (Sigma), dipalmitoylphosphatidyl-choline (Nattermann Phospholipids) and dimyristoylphosphatidylglycerol sodium salt in molar proportions of 5:4:1 are dissolved in 50 μl of absolute ethanol. The solution is injected via a Hamilton syringe into 2 ml of an aqueous solution containing 4 mg/ml of jack bean urease, where appropriate buffered with PBS buffer diluted to ⅒. The preparation is kept stirring at 45° C.

On contact with water, the lipids organize spontaneously in the form of liposomes (predominantly unilamellar liposomes of average size 50–100 nm), trapping a certain volume of urease solution.

These liposomes are purified (isolated from excess free urease) by gel filtration through a column of Sepharose CL-4B (Pharmacia). The degree of encapsulation of the urease, measured using iodine-125-labelled urease (Enzymobeads™ technique, Biorad), varies from 3 to 6%. If necessary, the liposome suspension is concentrated by ultrafiltration in a Novacell™ cell (Filtron) possessing an exclusion limit of 10 kD.

2. Extrusion 16.4 mg of a lipid mixture composed of cholesterol (Sigma), dipalmitoylphosphatidyl-choline (Nattermann Phospholipids) and dimyristoylphosphatidylglycerol sodium salt in molar proportions of 5:4:1 are dissolved in 4 ml of chloroform in a 25 ml round-bottomed pyrex flask. The solution is evaporated (Buchi Rotavapor) to form a thin lipid film on the walls of the flask. The lipid film is dried under a high vacuum for 2 hours and then taken up with 2 ml of water containing 8 mg of jack bean urease. After 4 hours of stirring at 45° C., the suspension is extruded (Extruder™, Lipex Biomembranes Inc., Vancouver) 5 times through 2 superposed polycarbonate membranes of porosity 400 nm (Nucleopore™, Costar) to form a homogeneous population of predominantly unilamellar liposomes approximately 400 nm in diameter containing urease. These liposomes are purified (isolated from excess free urease) by gel filtration through a column of Sepharose CL-4B (Pharmacia). The degree of encapsulation of the urease, measured using iodine-125-labelled urease (Enzymobeads™ labelling technique, Biorad), varies from 5 to 10%. If necessary, the liposome suspension is concentrated by ultrafiltration in a Novacell™ cell (Filtron) possessing an exclusion limit of 10 kD.

3. Microfluidizer method 82 mg of lipid mixture composed of cholesterol, dipalmitoylphosphatidylcholine and dimyristoylphosphatidylglycerol sodium salt in molar proportions of 5:4:1, obtained by lyophilization of an ethanolic solution (D3F —France), are taken up with 10 ml of 10 mM Hepes buffer, 150 mM NaCl, pH 7.4 containing 3.6 mg/ml of the recombinant apoenzyme form of $H.$ $pylori$ urease. After 4 hours of stirring at 45° C., the suspension is microfluidized by 5 runs at 500 kPa in an M110S microfluidizer (Microfluidics Co.) to form a homogeneous population of predominantly unilamellar liposomes approximately 100 nm in diameter containing urease. These liposomes are purified by gel filtration (column of Sepharose CL-4B, Pharmacia). The degree of encapsulation of the urease, measured by protein assay using the Micro BCA kit (Pierce) is 14.5%. If necessary, the liposome suspension is concentrated by ultrafiltration in a Novacell cell (Filtron) possessing an exclusion limit of 10 kD.

2.A.c) urease in liposomes with MPLA as adjuvant

When liposomes are prepared, MPLA (extracted from $E.$ $coli,$ Sigma) may be added to the lipid mixture, in the proportion of 1, 2 or 5% relative to the mass of lipid.

2.B. Immunization protocol

Two immunization protocols are tested. They are:

1) subcutaneous (aluminium))/[oral (intragastric)+nasal] (liposomes)

2) subcutaneous (liposomes)/[oral (intragastric)+nasal] (liposomes)

OF1 mice receive via the subcutaneous route:
either 20 μg of urease with aluminium as adjuvant as described in Section 2.A.a), in a final volume of 500 μl,
or 20 μg of urease in a liposomal preparation as obtained in Section 2.A.b), in a volume of 500 μl.

28 days after the subcutaneous injection, the mice receive simultaneously:

via the oral (intragastric) route, 20 μg of urease in a liposomal preparation as obtained in section 2.A.b), in a volume of 500 μl; and via the nasal route, 20 μg of urease in a liposomal preparation as obtained in section 2.A.b), in a volume of 50 μl.

15 days after the booster, the stomach and the salivary glands of the mice are removed; the cells are extracted according to the protocol described in the preamble to the examples and the IgA response is subjected to Elispot analysis according to the method described in the preamble.

Figure 3A:
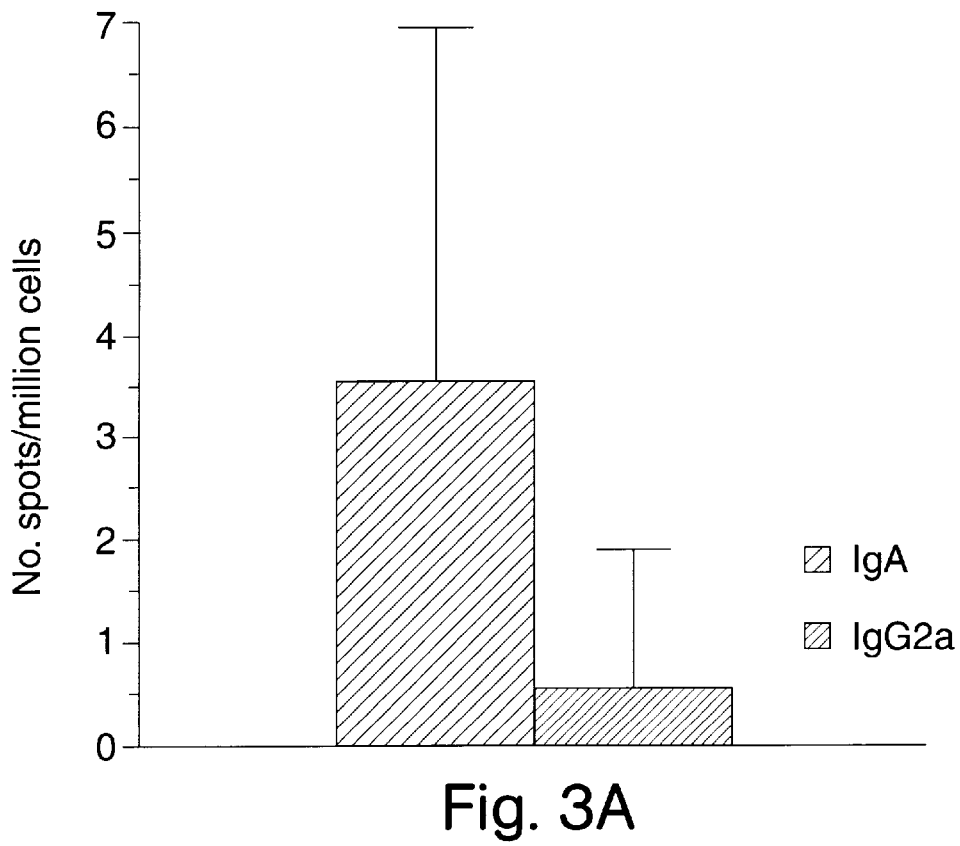
Figure 3B:
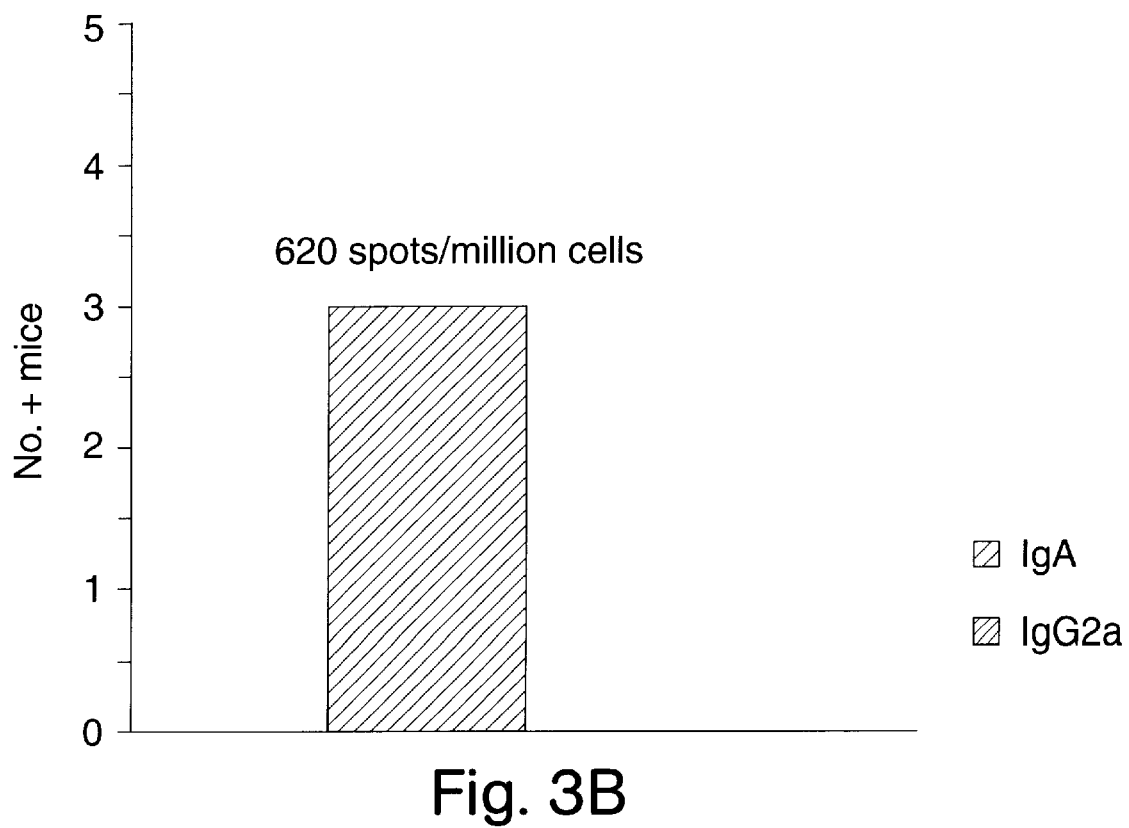
Figure 4A:
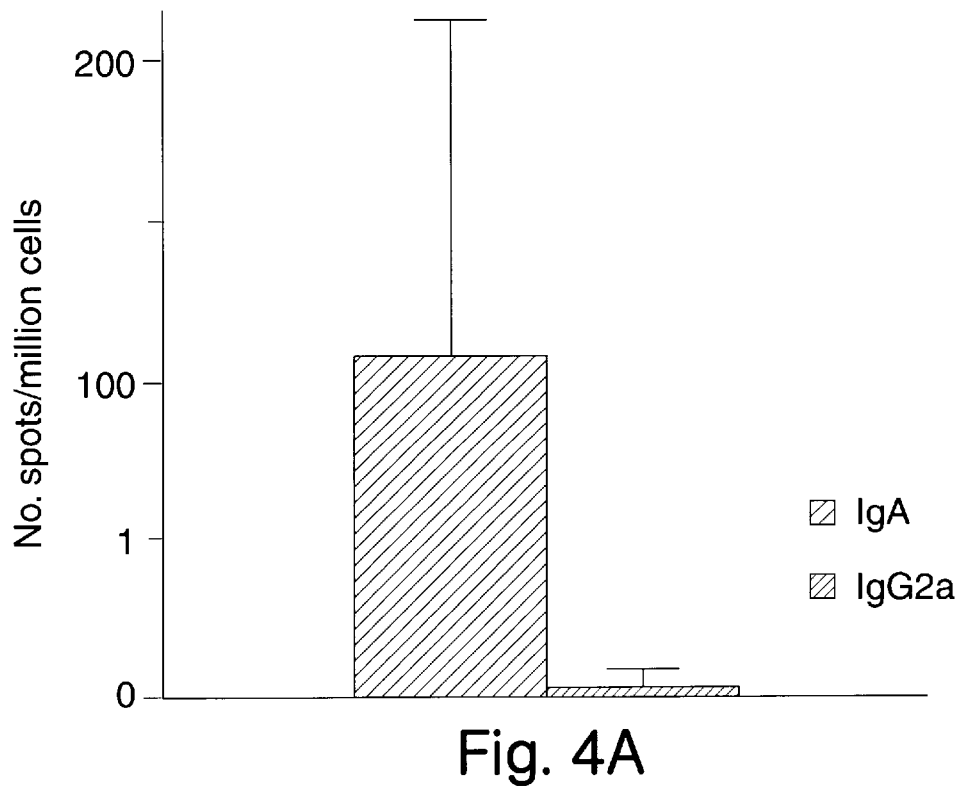
Figure 4B:
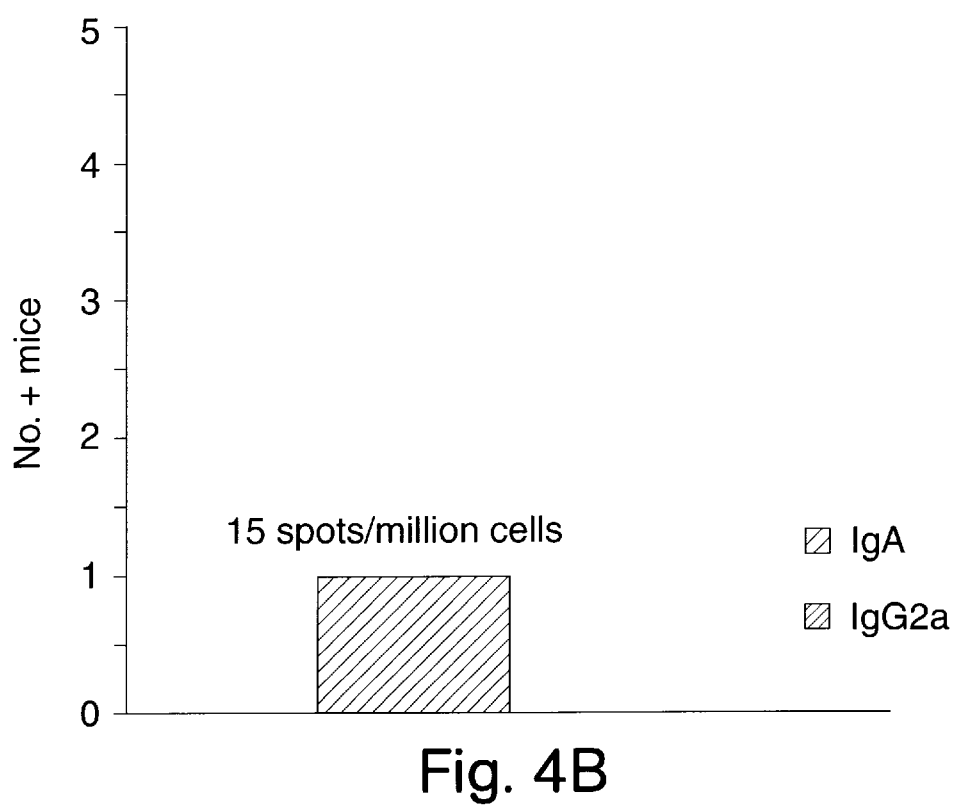

The results are presented in FIGS. 3 and 4. FIG. 3 shows that, in the case of the subcutaneous (aluminium)/[oral (intragastric)+nasal] (liposomes) protocol, the IgA response in the salivary glands (3A), though weak, is predominant, while, as regards the stomach (3B), 3 mice out of 5 respond to the immunization with a high number of spots.

FIG. 4 shows that, in the case of the subcutaneous (liposomes)/[oral+nasal] (liposomes) protocol, the response is very good in the salivary glands (4A) while it is weak in the stomach (4B). This suggests that, besides the protocol used, the formulation of the antigen is of importance.

EXAMPLE 3

Vaccination kit for *H. pylori* infections

Three preparations containing the apoenzyme of *H. pylori* urease, each formulated in a different way depending on the method of administration envisaged, are brought together in a kit.

3.A. Preparation of the apoenzyme

From one of the plasmids described in Labigne et al. (supra) (pILL914), a fragment coding for the N-terminal portion of UreA (up to the internal HindIII site), and containing a BspHr site at the translation initiation codon of UreA, is generated by PCR using the primers OTG5973 and OTG5974.

BspHI

OTG5973: CCAAATC ATG AAA CTC ACC CCA AAA GAG TTA Met Lys Leu Thr Pro Lys Glu Leu GAT AAG TTG
Asp Lys Leu

HindIII

OTG 5974: GCTTCTACATAGTTAAGCTTAATGCCTT

Figure 5:
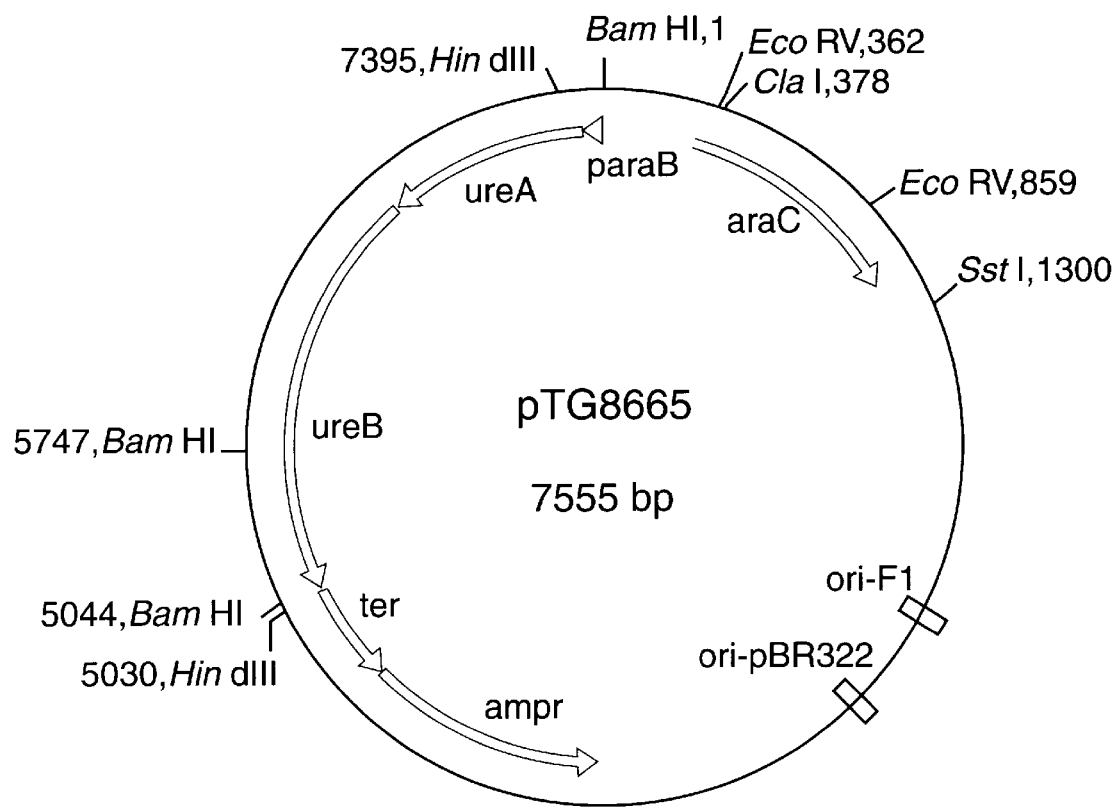
FIG. 5 depicts the plasmid pTG8665, used to produce the apoenzyme of *H. pylori* urease.

The fragment generated by PCR is digested with BspHI and HindIII and inserted simultaneously with the 2.35-kb HindIII fragment of pILL-914 carrying the 3' portion of ureA and of ureB into the vector pTG3704 digested with NcoI and HindIII, to give the plasmid pTG8665 as shown in FIG. 5. This plasmid carries the ureA and ureB genes fused to the araB promoter. The vector pTG3704 is described in European Patent Application EPA 584,266 published on 9th March 1994. This vector is derived from the plasmid para13 (Cagnon et al., Prot. Eng. (1991) 4 : 843) by destruction of the SphI site by treatment with Klenow polymerase.

I E. colistrain Xac-I (Normandy et al., PNAS (1986) 83 : 6548) is transformed with plasmid pTG8665. The transformed strain is cultured in LB medium supplemented with 100 μg/ml of ampicillin. In the exponential growth phase, 0.2% of arabinose is added for the purpose of inducing the expression of ureA and ureB. After various induction times (1 to 3 hours), the level of production of UreA and UreB is very high (approximately 10% of the total proteins), and the cells are then removed.

220 g of cells are recovered by centrifugation from 2.5 1 of cultures.

These cells are taken up in approximately 1 liter of 20 mM sodium phosphate buffer, pH 7.5 containing 175 mg of PMSF (1 mM). 4 μl of a benzonase solution at a concentration of 250 U/μl (Merck; ref. 1654), equivalent to 1 unit/ml final, as well as 1 ml of 1M $MgCl_2$ solution, are then added to the cell suspension. Reaction is allowed to proceed for 30 min.

The suspension is then introduced into a Rannie apparatus (high pressure homogenizer) and subjected to a pressure of 1,000 bars for 1 h in order to rupture the cells.

The choice may then be made between two alternative methods of purification.

3.A.a) First method

The rupturing of the cells is monitored by optical density. When the OD is of the order of 2.5–2, the suspension is removed from the apparatus and supplemented with 1 ml of 0.5M EDTA solution. It is centrifuged for 2 hours at 10,000 rpm, and the supernatant is then recovered and centrifuged at 100,000×g for 1 hour in order to remove the membranes.

The purification is carried out according to a protocol similar to the one described by Hu et al., Infect. Immun. (1992) 60 : 2657. The supernatant containing the soluble proteins is adjusted to pH 6.8 and then loaded at a flow rate of 4 ml/min onto an anion exchange column (DEAE-Sepharose, Pharmacia) of volume 5 cm×25 cm equilibrated with 20 mM $KPO_4$ buffer, pH 6.8 containing 1 mM PMSF (PO buffer). The column is eluted with a linear gradient of KCl from 0 to 0.5M. 14-ml fractions are collected and analysed by SDS-PAGE. Fractions containing urease in the purest form are pooled.

KCl is added to the fraction thereby obtained so that the final KCl concentration is equal to 1M, and the solution is loaded onto a column of phenyl-Sepharose (Pharmacia). The column is eluted with a gradient of KCl from 1M to 0M. As before, the fractions are collected and analyzed by SDS-PAGE. Fractions containing urea in the purest form are pooled and dialysed against 20 mM $KPO_4$ buffer, pH 7.5.

The fraction obtained is loaded onto an anion exchange column (Q-Sepharose Fast Flow; Pharmacia) equilibrated with 20 mM $KPO_4$ buffer, pH 7.5; as before, the column is eluted with a linear gradient of KCl from 0 to 0.5M and the fractions are collected and analyzed by SDS-PAGE.

Fractions containing urea are pooled and concentrated by diafiltration across a membrane whose cut-off threshold is 100 kDa, and the fraction is applied to a gel filtration column (Sephacryl 400 HR) equilibrated in 20 mM $NaPO_4$ buffer, pH 7.5; after analysis of the different fractions by SDS-PAGE, those containing urease are collected and concentrated by diafiltration across a membrane whose cut-off threshold is 100 kDa, and the solution is filtered through a membrane of porosity 0.22 μm. Sterile sucrose solution is added to the urease solution to obtain a final concentration of 2%. The solution is then lyophilized and is stored in this form while awaiting the subsequent steps.

3.A.b) Second method

This supernatant is adjusted to pH 7.5, and then loaded at a flow rate of 4 ml/min onto an anion exchange column (Q-Sepharose Fast Flow; Pharmacia; ref. 17-0510-01) of volume 5 cm×25 cm equilibrated with a 20 mM $KPO_4$ equilibrium buffer, pH 7.5 containing 1 mM PMSF. The column is eluted with a linear gradient of KCl from 0 to 0.5M in the equilibrium buffer (gradient vol.: 2.25 1 flow rate: 4 ml/min).

14-ml fractions are collected and analyzed by SDS-PAGE. The cleanest fractions are collected and pooled (these are, in general, fractions 82 to 121 starting from the beginning of the gradient).

The Q-Sepharose pool is loaded at a flow rate of 2 ml/min onto a column of zinc chelate (Chelating Sepharose Fast Flow; Pharmacia; ref. 17-0575-02) of volume 2.6 cm×11 cm, prepared beforehand as follows.

The column is loaded with metal with 2 volumes of 0.2M $ZnCl_2$ solution, and then rinsed with 3 volumes of 0.5M NaCl and thereafter with 3 volumes of a 50 mM Tris-HCl equilibration buffer, pH 8 containing 0.5M NaCl, 1 mM imidazole and 1 mM PMSF. The column is washed with 1 volume of the equilibration buffer containing 10 mM imidazole and then rinsed with 3 volumes of the equilibrium buffer containing 1 mM imidazole.

When loading is complete, the column is washed with the equilibration buffer until the washings return to the baseline value (washing carried out overnight at 0.2 ml/min).

The column is then washed with 200 ml of equilibration buffer containing 7.5 mM imidazole at a flow rate of 1 ml/min.

Elution takes place in a linear gradient of imidazole from 7.5 mM to 30 mM in the equilibration buffer (gradient volume: 250 ml; flow rate 1 ml/min).

10-ml fractions are collected and analyzed by SDS-PAGE. Fractions containing pure urease are collected and pooled (these are, in general, fractions 19 to 30 starting from the beginning of the gradient).

The Chelating Sepharose pool is then concentrated to 25 ml by ultrafiltration across an Amicon YM100 membrane.

This concentrate is then loaded onto a column of Sephacryl S-300 (Pharmacia; ref. 17-0599-01) of volume 2.6 cm×96 cm equilibrated in 20 mM $KPO_4$ buffer, 0.15M NaCl, pH 7.5.

Chromatography is performed at a flow rate of 0.5 ml/min. 10-ml fractions are recovered and analyzed by SDS-PAGE. Fractions containing pure urease are pooled (these are, in general, fractions 21 to 27 from the end of loading) and concentrated to approximately 2.5 mg/ml by ultrafiltration across an Amicon YM100 membrane. The apoenzyme preparation is filtered through a membrane of porosity 0.22 μm, and is stored frozen at −20° C. or lyophilized in the presence of sucrose, for example.

The preparations of the kit are as follows:

3.B. Apoenzyme with aluminium as adjuvant for administration via the subcutaneous route A dose for injection is prepared by adsorbing 20 μl of the apoenzyme solution obtained in 3.A. (equivalent to 50 μg) with 250 μl of a 1 mg/ml aluminium hydroxide preparation (alhydrogel; Superfos); after adsorption for 2 h at +4° C., the final volume is adjusted to 500 μl by adding PBS.

3.C. Apoenzyme in liposomes, for administration via the nasobuccal route, in aerosol form The apoenzyme form of *H. pylori* urease is encapsulated in liposomes. These liposomes have an average diameter of 100 nm and a protein content of 60 μg/mg of lipid.

A total amount of 0.1 mg of formulated urease is administered via the nasobuccal route. An aerosol can with two nozzles (nose and mouth) of the type marketed by the company VALOIS (Le Prieuré, BPG, 27110 Le Neubourg) is used.

Pumps allow a finite volume to be delivered, depending on the type of pump, a nozzle of variable size fitting onto the container equipped with its pump (not more than 300 μl per administration, it being possible for this dose to be repeated at chosen time intervals).

3.D. Apoenzyme in liposomes for intragastric administration

A total amount of 0.5 mg of formulated urease is administered via the intragastric route. The apoenzyme is prepared according to the method described in section 3.C., then lyophilized and taken up with 20 ml of 200 mM bicarbonate solution.

3.E. Immunization protocol

An adult receives subcutaneously the dose prepared in 3.B. 28 days after the primary injection, he receives via the nasobuccal route the dose prepared in 3.C. and ingests on the same day the dose prepared in 3.D.

EXAMPLE 4

Vaccination kits for *H. pylori* infections (DNA coding for the urease subunit ureB, used as vaccinating agent)

4.A. Construction of the plasmid vectors

Figure 6:
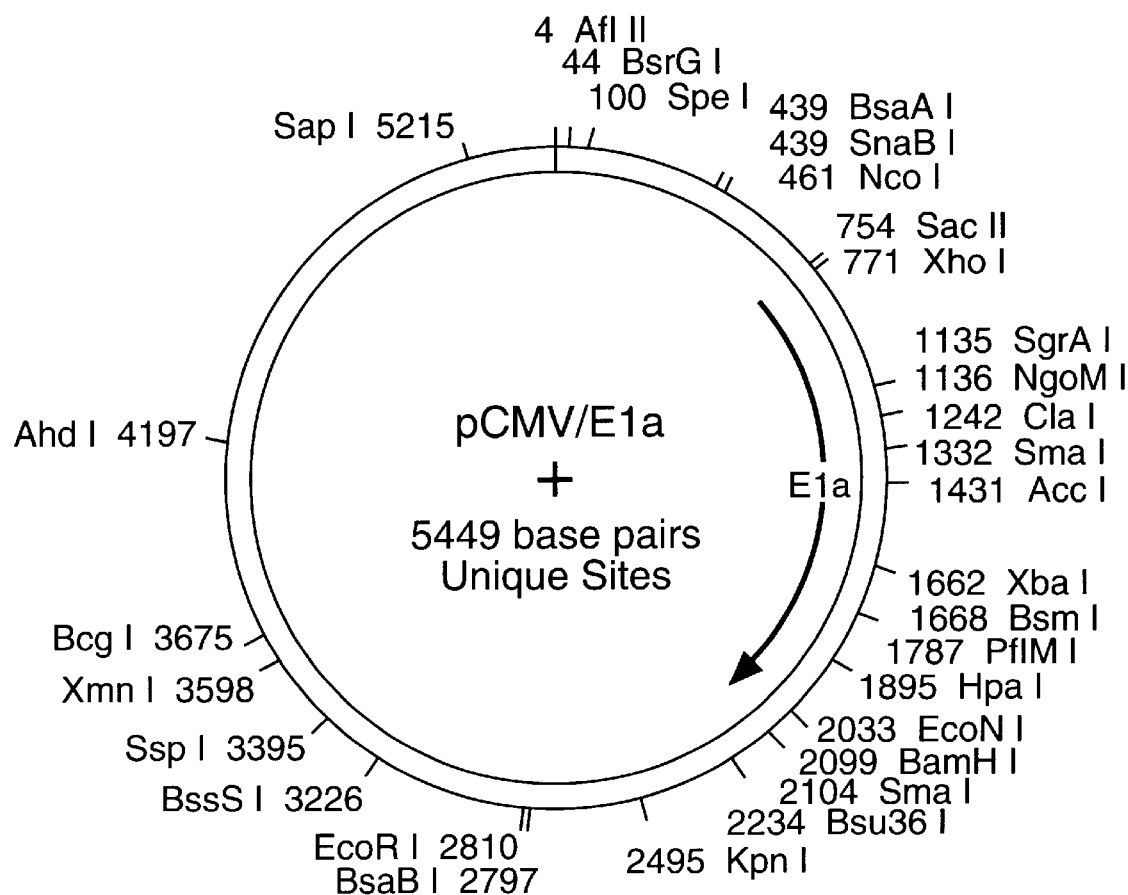
FIG. 6 depicts the plasmid pCMC/E1a in which the HindIII (1)—SacII (754) fragment contains the hCMV promoter, the XhoI (771)—SmaI (2104) fragment contains the E1a ORF, the SmaI (2104)—EcoRI (2810) fragment contains the BGH 3' end and the EcoRI (2810)—HindIII (1) fragment corresponds to the pUC19 skeleton.

The eukaryotic expression vector pCB-11 is constructed from the following three elements:

Plasmid pUC19 (commercially available) previously digested with XbaI and EcoRI;

a SpeI-SacII fragment isolated from plasmid pCMV/E1a (FIG. 6), which contains the early promoter of human cytomegalovirus (hCMV) as described in, e.g., U.S. Pat. No. 5,168,062; and a SacII-EcoRI fragment containing the 3' portion of the bovine growth hormone gene including the mRNA polyadenylation signal as well as the mRNA stabilization sequences. This SacII-EcoRI fragment is obtained from the plasmid pBS-BGH, constructed by inserting a BamHI-EcoRI fragment originating from plasmid pCMV/E1a into the Bluescript plasmid (commercially available).

Figure 7A:
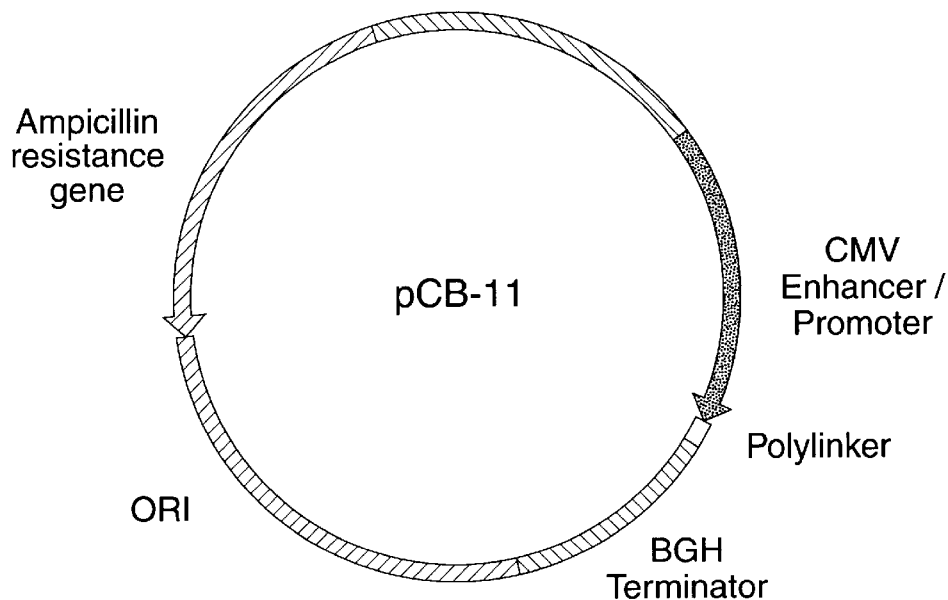
FIG. 7 depicts the plasmid pCB-11 (FIG. 7A) and a restriction map of pCB-11 (FIG. 7B).
Figure 7B:
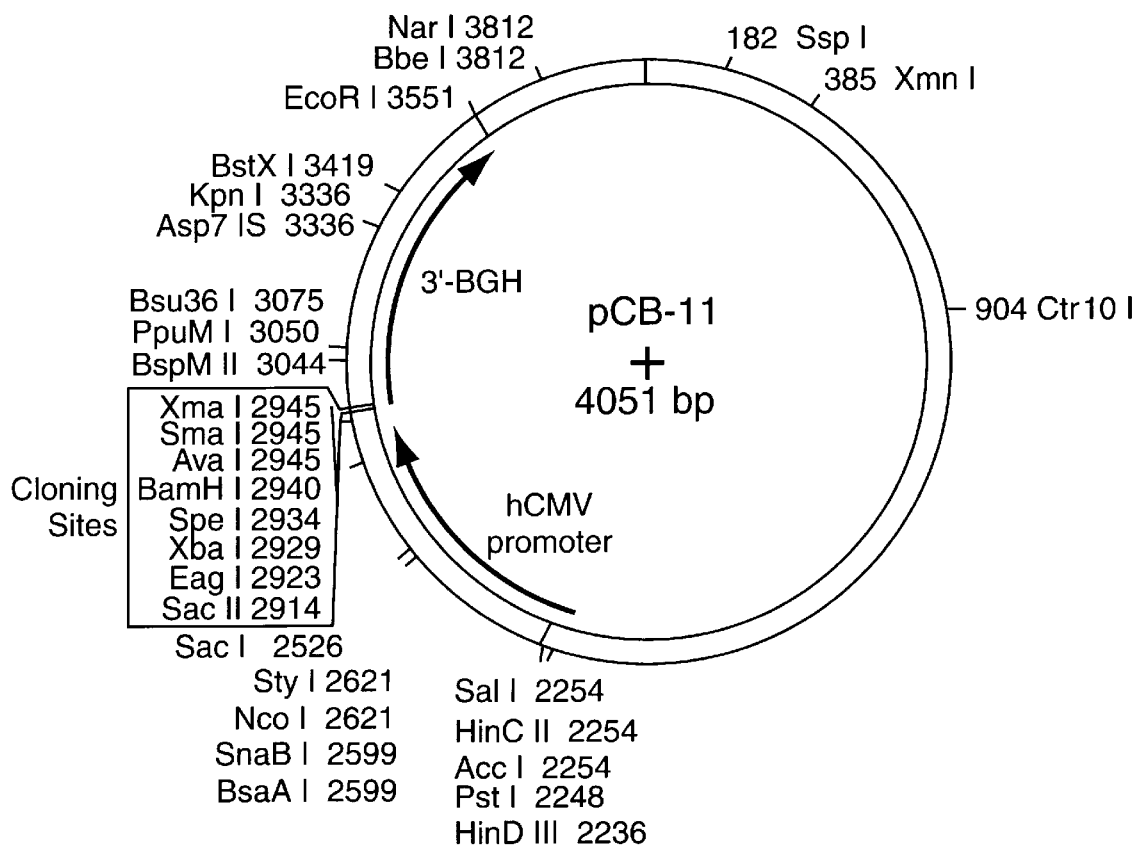

These three fragments are ligated together to form plasmid pCB-11 (FIG. 7).

The ureB gene is amplified by PCR from plasmid pILL914 and using the following primers:

upstream primer:

5' cgtctcgagccaccatgaaaaagattagcagaaag downstream primer:

5' atcgtcccgggcaggcctcttagaaaatgctaaagagttgcgccaagct.

Figure 8:
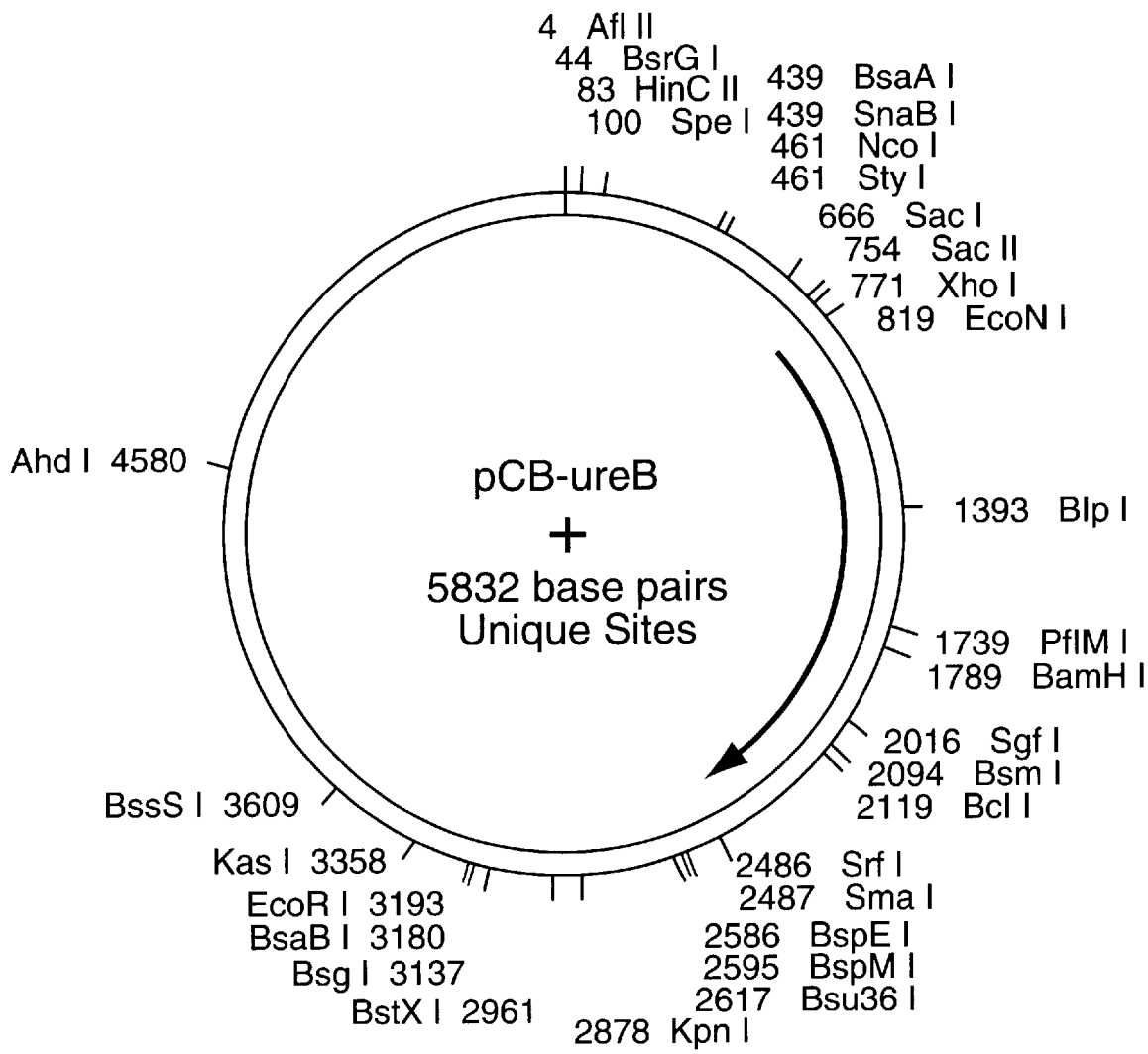
FIG. 8 depicts the plasmid pCB-ureB in which the ureB ORF extends from nucleotide 777 to nucleotide 2487.

The upstream primer enables the XhoI restriction site and the Kozak sequence to be introduced upstream of the open reading frame (ORF) of ureB, while the downstream primer enables the SmaI site to be introduced downstream of the ORF. The fragment generated by PCR is digested and then inserted into plasmid PCB-11 previously digested with XhoI and SmaI, to generate plasmid pCB-ureB (FIG. 8).

*E. coli* XL1 is transformed with this plasmid and then cultured according to conventional techniques. The plasmid thus amplified is harvested in a standard manner by alkaline lysis followed by an isopycnic caesium chloride gradient. The DNA is taken up either in distilled water or in physiological saline (0.9% NaCl).

4.B. Preparation of a liposome/DNA composition

O,O',O"-Tridodecanoyl-N-(ω-trimethylammoniododecanoyl) tris (hydroxymethyl) aminoethane bromide (commonly known as TC1–12) is manufactured according to the method described by Kunitake et al., J. Am. Chem. Soc. (1984) 106 : 1978. 10 mg of this product are then dissolved in 50 μl of ethanol. This preparation is then injected rapidly using a Hamilton syringe into 2 ml of deionized water with stirring at 42° C.

Liposomes approximately 50 nm in diameter form spontaneously during the dissolution of the ethanol in water. A liposomal preparation containing 5.2 mM TC1–12 is thereby obtained.

100 μl of the preparation obtained above are diluted by adding 150 μl of distilled water. 250 μl of an aqueous preparation of plasmid pCB-ureB at a concentration of 2 μg/μl are then added. The load ratio (TC1–12/nucleotide) is of the order of 0.35.

4.C. Immunization protocols 6- to 8-week-old Balb/c mice are previously anaesthetized by injection of a xylazine+ketamine mixture. They receive 3 administrations of 50 μg of pCB-ureB at 3-week intervals.

In the various immunization protocols, the intranasal (IN) route, the intramuscular (IM) route and the intradermal (ID) route are used.

For administration via the intranasal route, 50 μl of a DNA solution at a concentration of 100 μg/ml into physiological saline or in a liposome/DNA mixture as obtained in 4.B. are applied dropwise in the nostrils.

For administration via the intramuscular route, 50 μl of a DNA solution at a concentration of 100 μg/ml in physiological saline are injected into the quadriceps using a Hamilton syringe equipped with a 29 gauge needle.

For administration via the intradermal route, 100 μl of a DNA solution at a concentration of 500 μg/ml are injected at 5 sites into the skin of the previously shaved back using a pneumatic jet injector (Mesoflash™ 10).

The various immunization protocols are as follows:

| Group | Primary administration (Day zero) | First booster (Day 21) | Second booster (Day 42) |
|---|---|---|---|
| 1 (15 mice) | Lipo-pCB ureB/IN | Lipo-pCB ureB/IN | Lipo-pCB ureB/IN |
| 2 (15 mice) | pCB ureB/IN | pCB ureB/IN | pCB ureB/IN |
| 3 (10 mice) | pCB ureB/IM | lipo-pCB ureB/IN | lipo-pCB ureB/IN |
| 4 (10 mice) | pCB ureB/ID | lipo-pCB ureB/IN | lipo-pCB ureB/IN |

On days 14, 35 and 56, serum samples are drawn from each of the mice. The production of anti-urease antibodies is tested for by ELISA (a purified soluble extract of *H. pylori* is used).

The results summarized in FIG. 9 show that the various immunization protocols enable a strong IgG response and a smaller IgA response to be induced.

EXAMPLE 5

Induction of a mucosal immune response against *H. pylori* urease

5.A. Preparation of the immunizing composition 0.8 g of DC-Chol and 2.4 g of dioleoylphosphatidycholine (DOPC) are added to 20 ml of chloroform in a 1 liter round-bottomed flask. This mixture is evaporated under vacuum so as to form a lipid film on the walls of the flask. This film is then dried under a high vacuum overnight.

The film is then taken up with 400 ml of a solution of apoenzyme at a concentration of 1.5 mg/ml (prepared as described in Example 3.A.) in 20 mM Hepes buffer, pH 6.2. The mixture is left stirring for 6 hours at room temperature.

The resulting suspension of multilamellar vesicles is then microfluidized by 10 runs at 500 kPa in an M110S microfluidizer (Microfluidics Co.) to form a homogeneous population of predominantly unilamellar liposomes approximately 100 nm in diameter containing the apoenzyme.

These liposomes are filtered through a Stenivex-HV filter (0.45 μ, Millipore) and then lyophilized after the addition of 20 g of sucrose.

The size of the liposomes measured by light scattering (Zetamaster, Malvern Instruments) is 148±52 nm. The degree of encapsidation of the apoenzyme is of the order of 20%; the remainder of the total amount being in free (non-encapsidated) form.

5.B. Immunization protocols 6- to 8-week-old Swiss mice are divided into 4 groups (10 mice/group) and receive on D0, D28 and D56, via various routes, a dose of the preparation obtained above.

Two immunization protocols are tested. They are:

1) subcutaneous/intragastric+nasal/intragastric+nasal; and 2) intragastric+nasal, repeated 3 times.

The doses are as follows: for administration via the nasal route, an amount of lyophilizate corresponding to 10 μg of total apoenzyme (encapsidated+non-encapsidated) is taken up immediately before use in 30 μl of physiological saline (0.9% NaCl). The dose is applied dropwise to the nostrils. For administration via the subcutaneous route, the same dose of lyophilizate is taken up with 300 μl of saline. For administration via the intragastric route, an amount of lyophilizate corresponding to 40 μg of total apoenzyme (encapsidated+non-encapsidated) is taken up with 300 μl of saline supplemented with 0.2M NaHCO$_3$. The dose is administered using a cannula coupled to a 1 ml syringe.

15 days after the last administration, the mice are challenged by intragastric gavage with $10^8$ microbes of an *H. pylori* strain adapted to mice. One month after challenge, the stomachs are removed and a test of urease activity (Jatrox ND) is performed on ¼ of the stomach. 4 hours after removal, the optical density of the medium is measured at 550 nm. The results are presented in FIG. 10.

These results show that, even though complete protection is not obtained at the doses of DC-Chol used, a significant reduction in urease activity, and hence in the infection, is observed compared to the positive controls (mice which have received empty liposomes). These results also demonstrate the advantage of a primary immunization via the parenteral route targeted in the dorsolumbar region (subcutaneous; the intramuscular route could have been used as well, and would advantageously have enabled the coeliac nodes to have been targeted more specifically).

What is claimed is:

1. A method for inducing in a mammal, an immune response against an antigen of a pathogen of the respiratory, gastrointestinal, or genitourinary tract at mucosal effector site, which comprises administering a second and a third inducing agent, to said mammal;

wherein said second and third inducing agents are selected independently from the group consisting of the antigen and, provided the antigen is a protein, an expression cassette capable of expressing the antigen in said mammal;

wherein said second inducing agent is administered concomitantly with or prior to the third inducing agent;

wherein said second inducing agent is administered by the nasal or buccal route so that the second inducing agent is targeted to the inducer site(s) for an immune response in the naso-oropharynx or the salivary glands; and wherein said third inducing agent is administered by a mucosal route other than the nasal route so that the antigen is targeted to the inducer site(s) for the immune response at the effector site at which the immune response is sought.

2. A method according to claim 1, wherein the antigen is a protein.

3. A method according to claim 2, wherein said inducing agent is selected from the group consisting of the antigen and an expression cassette comprising DNA encoding the antigen.

4. A method according to claim 1, wherein the third product is formulated for pulmonary administration.

5. A method according to claim 1, wherein the third product is formulated for urogenital administration.

6. A method according to claim 1, wherein the third product is formulated for oral administration.

7. A method according to claim 6, wherein the antigen is *Heliiobacter pylori* antigen.

8. A method according to claim 7, wherein the antigen is the apoenzyme form of *H. pylori* urease.

9. A method according to claim 1, wherein the third product is formulated for intragastric administration.

10. A method according to claim 9, wherein the antigen is *Helicobacter pylori* antigen.

11. A method according to claim 10, wherein the antigen is the apoenzyme form of *H. pylori* urease.

12. A method according to claim 1, wherein the first product further comprises an adjuvant selected from the group consisting of aluminum hydroxide, aluminum phosphate, and ISCOMs.

13. A method according to claim 1, wherein the second product comprises particles selected from the group consisting of liposomes and microspheres.

14. A method according to claim 13, wherein the particles are from about 0.05 µm to about 5 µm in diameter.

15. A method according to claim 1, wherein the third product comprises particles selected from the group consisting of liposomes and microspheres, and further wherein said third product is formulated for pulmonary, oral, or intragastric administration.

16. A method according to claim 15, wherein the third product comprises particles from about 0.05 to about 5 µm in diameter, and is formulated for pulmonary administration.

17. A method according to claim 16, wherein the second or third product is a spray or an aerosol.

18. A method according to claim 15, wherein the third product comprises particles from about 0.05 to about 5 µm in diameter, and is formulated for oral or intragastric administration.

19. A method according to claim 1, wherein the third product is an enterically protected preparation.

20. A method according to claim 1, wherein the second or third product further comprises a non-toxic adjuvant, other than the non-toxic subunits or the detoxified forms of bacterial toxins and other than liposomes or microspheres.

21. A method according to claim 1, wherein the second or third product further comprises the major lipopolysaccharide antigen of a bacteria.

22. A method according to claim 1, wherein the inducing agent contained in the first, the second or the third product is the antigen.

23. A method according to claim 1, wherein the inducing agents contained in the second and third products are the same.

24. A method according to claim 1, wherein the inducing agents contained in the first, second and third products are the same.

25. A method according to claim 1, wherein the antigen is pathogenic for the mammal.

26. A method according to claim 11, which comprises administering a first inducing agent to said mammal by the systemic route; said first inducing agent being selected from the group consisting of the antigen and, provided the antigen is a protein, an expression cassette capable of expressing the antigen in a mammal.

27. A method according to claim 2, wherein the first product is formulated for parenteral administration.

28. A method according to claim 27, wherein the first product is formulated for subcutaneous, intradermal or intramuscular administration.

* * * * *